United States Patent
Dymek et al.

(10) Patent No.: US 10,138,247 B2
(45) Date of Patent: Nov. 27, 2018

(54) 7-(MORPHOLIN-4-YL)PYRAZOLE[1,5-A] PYRIMIDINE DERIVATIVES AS PI3 KINASE INHIBITORS

(71) Applicant: CELON PHARMA S.A., Kielpin/Lomianki (PL)

(72) Inventors: Barbara Dymek, Czeladz (PL); Marcin Zagozda, Warsaw (PL); Maciej Wieczorek, Kielpin/Lomianki (PL); Krzysztof Dubiel, Warsaw (PL); Aleksandra Stanczak, Warsaw (PL); Daria Zdzalik, Zwolen (PL); Pawel Gunerka, Warsaw (PL); Mariola Sekular, Mrozy (PL); Maciej Dziachan, Warsaw (PL)

(73) Assignee: CELON PHARMA, S.A., Kielpin/Lomianki (PL)

( * ) Notice: Subject to any disclaimer, the term of this patent is extended or adjusted under 35 U.S.C. 154(b) by 0 days.

(21) Appl. No.: 15/562,537

(22) PCT Filed: Mar. 30, 2016

(86) PCT No.: PCT/IB2016/051792
§ 371 (c)(1),
(2) Date: Sep. 28, 2017

(87) PCT Pub. No.: WO2016/157091
PCT Pub. Date: Oct. 6, 2016

(65) Prior Publication Data
US 2018/0111939 A1   Apr. 26, 2018

(30) Foreign Application Priority Data

Apr. 2, 2015   (PL) .......................... 411864

(51) Int. Cl.
*C07D 487/04* (2006.01)
*C07D 413/14* (2006.01)
(Continued)

(52) U.S. Cl.
CPC ............ *C07D 487/04* (2013.01); *A61P 29/02* (2018.01); *A61P 35/00* (2018.01); *A61P 37/00* (2018.01);
(Continued)

(58) Field of Classification Search
CPC .. C07D 487/04; C07D 413/14; C07D 417/14; A61K 31/519; A61K 31/5375; A61K 31/554
(Continued)

(56) References Cited

FOREIGN PATENT DOCUMENTS

WO   09053716   4/2009
WO   10136491   12/2010
(Continued)

OTHER PUBLICATIONS

Blunt et al. Leukemia Research Reports 4 (2015) 60-63.*
(Continued)

*Primary Examiner* — Venkataraman Balasubramanian
(74) *Attorney, Agent, or Firm* — Gary J. Gershik; Cooper & Dunham LLP

(57) ABSTRACT

A compound of the general formula (I) wherein Y represents —$CH_2$— or >C=O; $R^1$ is selected from the group consisting of A1, A2 and A3; $R^2$ represents dioxothiomorpholino moiety B1, piperazinyl moiety B2, azetidinyl moiety B3, or piperidinyl moiety B4; $R^3$ is selected from the group consisting of H, halogen, and C1-C4 alkyl; $R^4$ is selected from the group consisting of C1-C4 alkyl, C3-C4-cycloalkyl, C1-C4 alkyl substituted with C1-C4 alkoxy, and $CHF_2$, and their pharmaceutically acceptable salts. Pharmaceutical compositions comprising said compounds and their use in the treatment of diseases of immune system, inflammatory diseases and cancer.

(I)

A1

A2

A3

B1

(Continued)

-continued

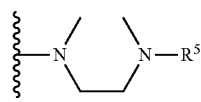

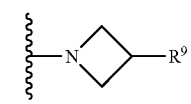

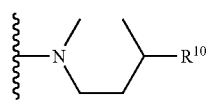

19 Claims, 2 Drawing Sheets

Figure 1:
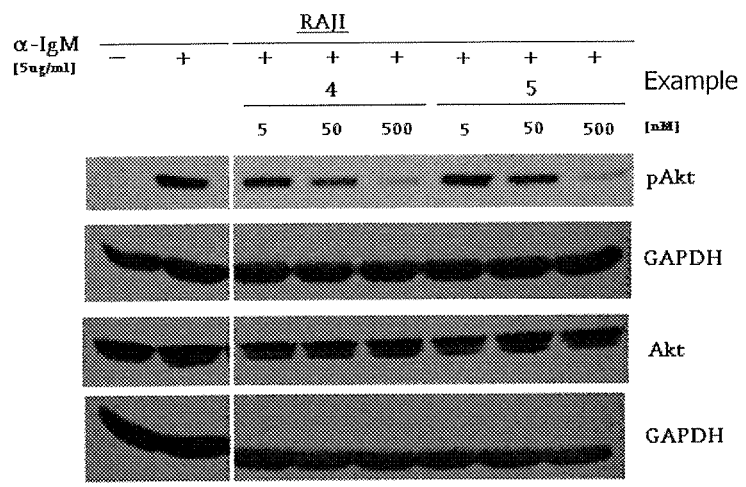

(51) Int. Cl.
C07D 417/14 (2006.01)
A61K 31/5375 (2006.01)
A61K 31/554 (2006.01)
A61P 35/00 (2006.01)
A61P 29/02 (2006.01)
A61P 37/00 (2006.01)
C07D 519/00 (2006.01)

(52) U.S. Cl.
CPC ......... C07D 413/14 (2013.01); C07D 417/14 (2013.01); C07D 519/00 (2013.01)

(58) Field of Classification Search
USPC ................ 544/117, 61; 514/234.2, 228.5
See application file for complete search history.

(56) References Cited

FOREIGN PATENT DOCUMENTS

WO 10138589 12/2010
WO 11101429 8/2011

OTHER PUBLICATIONS

Golub et al., Science, 286, 531-537, 1999.*
Freshney et al., Culture of Animal Cells, A Manual of Basic Technique, Alan R. Liss, Inc., 1983, New York, p. 4.*
Dermer et al., Bio/Technology, 1994, 12:320.*
Cohen et al., Current Opinion in Chemical Biology, 3,459-465, 1999.*
Cecil Textbook of Medicine, edited by Bennet, J.C., and Plum F., 20th edition, vol. 1, 1004-1010, 1996.*
PCT International Publication No. WO 2009/053716 A1, (F. Hoffmann-La Roche AG) published Apr. 30, 2009 (Exhibit 1).
PCT International Publication No. WO 2010/136491 A1, (F. Hoffmann-La Roche AG) published Dec. 2, 2010 (Exhibit 2).
PCT International Publication No. WO 2010/138589 A1, (Genentech, Inc.) published Dec. 2, 2010 (Exhibit 3).
PCT International Publication No. WO 2011/101429 A1, (F. Hoffmann-La Roche AG) published Aug. 25, 2011 (Exhibit 4).
International Search Report issued by the International Searching Authority (ISA/O.E.P.M.) dated Jun. 9, 2016 in connection with International Application No. PCT/IB2016/051792 (Exhibit 5).

* cited by examiner

7-(MORPHOLIN-4-YL)PYRAZOLE[1,5-A]PYRIMIDINE DERIVATIVES AS PI3 KINASE INHIBITORS

RELATED APPLICATIONS

This application is a § 371 national stage of PCT International Application No. PCT International Application No. PCT/IB2016/051792, filed Mar. 30, 2016, designating the United States, and claiming priority of Polish Patent Application No. PL411864, filed Apr. 2, 2015, the contents of each of which are hereby incorporated by reference into this application.

The present invention relates to novel 7-(morpholin-4-yl)pyrazolo[1,5-a]pyrimidine derivatives, pharmaceutical compositions containing them, and their use as medicaments. 7-(Morpholin-4-yl)pyrazolo[1,5-a]pyrimidine derivatives exhibit the ability to inhibit PI3 kinase activity and can find use as medicaments, especially for treating immune system diseases, inflammatory diseases and cancer.

PI3 family of kinases are responsible for signal transduction on one of critical signaling pathways, responsible for regulation of cell survival, differentiation and migration processes. These kinases are also responsible for regulation of immune system function. Aberrant activation of PI3K pathway has been confirmed in oncological diseases, such as chronic lymphocytic leukemia or non-Hodgkin lymphoma, as well as in diseases with underlying inflammatory processes, such as for example rheumatoid arthritis or asthma.

Active kinases PI3 are composed of a catalytic subunit and a regulatory subunit. PI3K type I family of kinases includes four regulatory subunits: PI3K-$\alpha$, -$\beta$, -$\gamma$, and -$\delta$. Isoforms $\alpha$ and $\beta$ are expressed in all tissues, and their inactivation at the embryonal development stage is lethal. Expression of isoforms $\gamma$ and $\delta$ is limited to hematopoietic line; their inactivation is not lethal, resulting rather in occurrence of immunodeficiency syndrome in developing organisms.

Lipid kinases PI3 catalyze production of phosphatidylinositol (3,4,5)-trisphosphate ($PIP_3$) by phosphorylation of phosphatidylinositol via phosphatidylinositol 3-phosphate (PIP) and phosphatidylinositol 3,4-bisphosphate intermediates. Phospholipid $PIP_3$ located in cellular membrane is a binding site for AKT protein, the degree of phosphorylation of which reflects the activity of PI3K pathway.

Therefore, inhibition of PI3K is the attractive mechanism of treatment of many diseases, wherein the level phosphorylation of AKT protein in cells may play role.

Because of expression of PI3K $\alpha$ and $\beta$ in a wide spectrum of tissues, as well as their role in embryonal development, non-selective PI3K inhibitors may have limited tolerability and high toxicity.

Therefore, a need exists of selective PI3K inhibitors, especially PI3K$\delta$ inhibitors, exhibiting desired activity and limited ability to cause adverse side effects.

Various lipid kinases PI3 inhibitors are disclosed in the prior art.

WO2010136491 and WO2010138589 disclose bicyclic indolopyrimidine compounds as exhibiting kinase PI3 inhibition activity and useful for treating diseases such as inflammatory and immunological disorders and cancers.

WO201110142 discloses morpholino-substituted pyrido[3,2-d]pyrimidine compounds as exhibiting kinase PI3 inhibition activity and useful for treating diseases such as inflammatory and immunological disorders and cancers.

The object of the invention is the provision of novel compounds, PI3K inhibitors of potential utility in the treatment of inflammatory and immunological diseases and disorders, and cancers, exhibiting selective activity targeted at specific PI3K isoforms, in particular PI3K delta.

The present invention relates to a compound of the general formula (I)

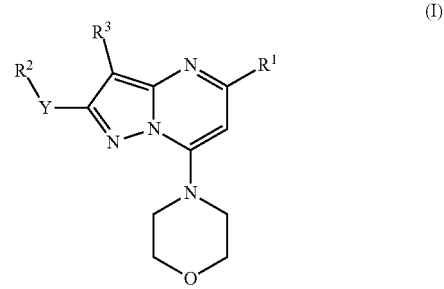

wherein:
Y represents —$CH_2$— or >C=P;
$R^1$ is selected from the group consisting of A1, A2 and A3:

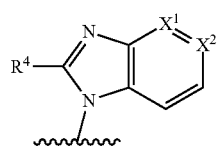

A1

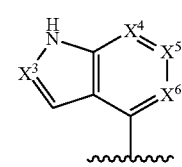

A2

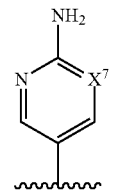

A3

$R^2$ represents:
  dioxothiomorpholino moiety B1;

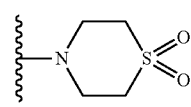

B1 piperazinyl moiety B2

B2 wherein two carbon atoms of the piperazine ring can be optionally joined by methylene bridge to form 2,5-diazabicyclic moiety, and $R^5$ is selected from the group consisting of —SO$_2$CH$_3$; —C(O)—C1-C3-alkyl; —C(O)—C3-C5-cycloalkyl; phenyl substituted with —O—C1-C3 alkyl; and —CR$^6$R$^7$R$^8$,
wherein R$^6$, R$^7$ and R$^8$ are independently selected from the group consisting of hydrogen atom, CH$_3$, cyclopropyl and CONH$_2$, with the proviso that only one of R$^6$, R$^7$ and R$^8$ may represent cyclopropyl or CONH$_2$,
or one of R$^6$, R$^7$ and R$^8$ represents hydrogen atom and remaining two of R$^6$, R$^7$ and R$^8$ are joined together to form —(CH$_2$)$_2$—, —(CH$_2$)$_3$—, —(CH$_2$)$_4$—, or —(CH$_2$—O—CH$_2$)—;
azetidinyl moiety B3

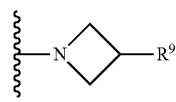

wherein R$^9$ is selected from the group consisting of morpholino, 2,6-dimethylomorpholino, 1,1-dioxothiomorpholino, 4,4-difluoropiperidinyl, and 3-methoxyazetidin-1-yl; or
piperidinyl moiety B4

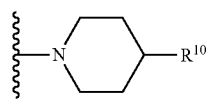

wherein R$^{10}$ is selected from the group consisting of C1-C4 alkyl; C1-C4 alkyl substituted with OH; —COO(C1-C3 alkyl); —N(C1-C3 alkyl)$_2$; —NHCONH—C1-C3-alkyl; —NHCONH—C1-C3-phenyl; piperazinyl; and piperazinyl substituted at the position 4 with C1-C3 alkyl;
R$^3$ is selected from the group consisting of H, halogen, and C1-C4 alkyl;
R$^4$ is selected from the group consisting of C1-C4 alkyl, C3-C4-cycloalkyl, C1-C4 alkyl substituted with C1-C4 alkoxy, and CHF$_2$;
X$^1$ and X$^2$ have the following meanings:
 (i) X$^1$ represents CH and X$^2$ represents CH or N;
 (ii) X$^1$ represents N and X$^2$ represents CH, or
 (iii) X$^1$ represents CH and X$^2$ represents C—O—CH$_3$;
X$^3$, X$^4$, X$^5$ and X$^6$ have the following meanings:
 (i) X$^3$ represents N, X$^4$ represents CH, X$^5$ represents CH, and X$^6$ represents CH;
 (ii) X$^3$ represents CH, X$^4$ represents N, X$^5$ represents CH, and X$^6$ represents CH;
 (iii) X$^3$ represents CH, X$^4$ represents CH, X$^5$ represents N, and X$^6$ represents CH;
 (iv) X$^3$ represents CH, X$^4$ represents CH, X$^5$ represents CH, and X$^6$ represents CH or CF; or
 (v) X$^3$ represents CH, X$^4$ represents CH, X$^5$ represents CF, and X$^6$ represents CH;
X$^7$ represents CH or N;
wavy line indicated the point of attachment;
and acid addition salts thereof.
In one embodiment, the invention relates to the compound of the formula (I), wherein Y represents —CH$_2$—.
In another embodiment, the invention relates to the compound of the formula (I), wherein Y represents >C=O.
One group of the compounds of the invention are the compounds of the formula (I), wherein R$^3$ represents H.

Another group of the compounds of the invention are the compounds of the formula (I), wherein R$^3$ represents C1-C4 alkyl. Advantageously, R$^3$ represents methyl.
Yet another group of the compounds of the invention is the compound of the formula (I), wherein R$^3$ represents halogen atom. Halogen atom encompasses chlorine, bromine and fluorine atoms, and advantageously represents chlorine atom.
In another embodiment of the compounds of the invention R$^2$ represents B1.
In another embodiment of the compounds of the invention R$^2$ represents B2.
Another sub-group of the compounds of the invention are the compounds of the formula (I), wherein R$^5$ in B2 represents —CR$^6$R$^7$R$^8$, and R$^8$, R$^6$, R$^7$ and R$^8$ are independently selected from the group consisting of hydrogen atom and CH$_3$, i.e. R$^5$ represents C1-C4 alkyl selected from the group consisting of CH$_3$, CH$_2$CH$_3$, CH(CH$_3$)$_2$, and C(CH$_3$)$_3$. Advantageously, R$^5$ represents C(CH$_3$)$_3$ (t-butyl).
In another embodiment of the compounds of the invention R$^2$ represents B3.
In another embodiment of the compounds of the invention R$^2$ represents B4.
In one variant of the compounds of the invention, R$^1$ represents A1 or A2.
In further embodiment, R$^1$ represents A1, wherein X$^1$ represents CH and X$^2$ represents CH or N.
In one sub-group of this variant, R$^1$ represents A1, wherein X$^1$ represents CH and X$^2$ represents CH or N, and R$^2$ represents B2 or B4. In particular, X$^1$ represents CH and X$^2$ represents CH. In an embodiment of such subgroup Y represents —CH$_2$—. Advantageously, R$^5$ in B2 moiety represents C1-C4 alkyl, especially t-butyl. Also preferably, R$^{10}$ in B4 moiety represents C1-C4 alkyl substituted with OH, especially 2-hydroxypropan-2-yl.
In another sub-group of this variant, R$^1$ represents A1, wherein X$^1$ represents CH and X$^2$ represents CH or N, and R$^2$ represents B3 and Y represents —CH$_2$—. In particular, X$^1$ represents CH and X$^2$ represents CH.
In another embodiment, R$^1$ represents A1, wherein X$^1$ represents N and X$^2$ represents CH, and R$^2$ represents B2 or B4. In a sub-group of this embodiment Y represents —CH$_2$—. Advantageously, R$^5$ in B2 represents C1-C4 alkyl, especially t-butyl. Also preferably, R$^{10}$ in B4 represents C1-C4 alkyl substituted with OH, especially 2-hydroxypropan-2-yl.
In another embodiment, R$^1$ represents A1, wherein X$^1$ represents CH and X$^2$ represents C—O—CH$_3$. In a sub-group of this embodiment, Y represents —CH$_2$—. Advantageously, R$^5$ in B2 represents C1-C4 alkyl, especially t-butyl. Also preferably, R$^{10}$ in B4 represents C1-C4 alkyl substituted with OH, especially 2-hydroxypropan-2-yl.
Advantageously, R$^4$ represents C1-C4 alkyl, including methyl, ethyl, n-propyl, iso-propyl, n-butyl, iso-butyl and t-butyl, especially methyl, ethyl or iso-propyl. Also preferably, R$^4$ represents cyclopropyl or cyclobutyl. Most preferably, R$^4$ is CHF$_2$.
In a further variant of the compounds of the invention R$^1$ represents A2.
In a sub-group of this variant, R$^1$ represents A2 wherein X$^3$ represents N, X$^4$ represents CH, X$^5$ represents CH, and X$^6$ represents CH, and R$^2$ represents B2 or B4. In an embodiment of this sub-group Y represents —CH$_2$—. Advantageously, R$^5$ in B2 represents C1-C4 alkyl, especially t-butyl. Also preferably, R$^{10}$ in B4 represents C1-C4 alkyl substituted with OH, especially 2-hydroxypropan-2-yl.

In another sub-group of this variant, $R^1$ represents A2 wherein $X^3$ represents CH, $X^4$ represents N, $X^5$ represents CH, and $X^6$ represents CH, and $R^2$ represents B2 or B4. In an embodiment of this sub-group Y represents —CH$_2$—. Advantageously, $R^5$ in B2 represents C1-C4 alkyl, especially t-butyl. Also preferably, $R^{10}$ in B4 represents C1-C4 alkyl substituted with OH, especially 2-hydroxypropan-2-yl.

In another sub-group of this variant, $R^1$ represents A2 wherein $X^3$ represents CH, $X^4$ represents CH, $X^5$ represents N, and $X^6$ represents CH, and $R^2$ represents B2 or B4. In an embodiment of this sub-group Y represents —CH$_2$—. Advantageously, $R^5$ in B2 represents C1-C4 alkyl, especially t-butyl. Also preferably, $R^{10}$ in B4 represents C1-C4 alkyl substituted with OH, especially 2-hydroxypropan-2-yl.

In another sub-group of this variant, $R^1$ represents A2 wherein $X^3$ represents CH, $X^4$ represents CH, $X^5$ represents CH, and $X^6$ represents CH or CF, especially CH, and $R^2$ represents B2 or B4. In an embodiment of this sub-group Y represents —CH$_2$—. Advantageously, $R^5$ in B2 represents C1-C4 alkyl, especially t-butyl. Also preferably, $R^{10}$ in B4 represents C1-C4 alkyl substituted with OH, especially 2-hydroxypropan-2-yl.

In another sub-group of this variant, $R^1$ represents A2 wherein $X^3$ represents CH, $X^4$ represents CH, $X^5$ represents CH and $X^6$ represents CH or CF, especially CH, and $R^2$ represents B2 or B4. Advantageously, $R^5$ in B2 represents C1-C4 alkyl, especially t-butyl. Also preferably, $R^{10}$ in B4 represents C1-C4 alkyl substituted with OH, especially 2-hydroxypropan-2-yl.

In another sub-group of this variant, $R^1$ represents A2 wherein $X^3$ represents CH, $X^4$ represents CH, $X^5$ represents CF and $X^6$ represents CH, and $R^2$ represents B2 or B4. Advantageously, $R^5$ in B2 represents C1-C4 alkyl, especially t-butyl. Also preferably, $R^{10}$ in B4 represents C1-C4 alkyl substituted with OH, especially 2-hydroxypropan-2-yl.

In a further variant of the compounds of the invention $R^1$ represents A3 moiety, and $R^2$ represents B2 or B4. Advantageously, $R^5$ in B2 represents C1-C4 alkyl, especially t-butyl. Also preferably, $R^{10}$ in B4 represents C1-C4 alkyl substituted with OH, especially 2-hydroxypropan-2-yl.

In one sub-group of the compounds of the invention $R^1$ represents A1 or A2, and $R^2$ represents B2 or B4.

Advantageously, $R^5$ in B2 represents tert-butyl.

Advantageously, $R^{10}$ in B4 represents 2-hydroxypropan-2-yl.

Unless specifically defined otherwise, the term C1-C4 alkyl used herein encompasses methyl, ethyl, n-propyl, iso-propyl, n-butyl, sec-butyl, and tert-butyl. The term C1-C3 alkyl encompasses methyl, ethyl, n-propyl, and iso-propyl.

The term C1-C4 alkoxy encompasses methoxy, ethoxy, n-propoxy, n-butoxy, sec-butoxy, and tert-butoxy.

The term C3-C4-cycloalkyl encompasses cyclopropyl and cyclobutyl, and the term C3-C5-cycloalkyl encompasses cyclopropyl, cyclobutyl, and cyclopentyl.

The compounds of the formula (I) of the invention exhibit the ability of PI3 kinase inhibition and can find use as medicaments, in particular for treating immune system diseases and disorders, inflammatory diseases and disorders, and cancer.

A specific characteristics of the compounds of the invention is high selectivity of kinase PI3K delta (PI3Kδ) inhibition in comparison with other isoforms of this kinase. This allows to expect reduced toxicity in comparison with broad spectrum inhibitors acting on many PI3K isoforms.

Further aspect of the invention is therefore the compound of the formula (I) as defined above for use as a medicament.

Yet further aspect of the invention is therefore the use of the compound of the formula (I) as defined above for the preparation of a medicament for the treatment of immune system diseases and disorders, inflammatory diseases and disorders, and cancer.

Another aspect of the invention is a pharmaceutical composition comprising the compound of the formula (I) as defined above and pharmaceutically acceptable excipients.

Another aspect of the invention is a method of treatment of immune system diseases and disorders, inflammatory diseases and disorders, and cancer, which comprises administering of an effective amount of the compound of the formula (I) as defined above.

Acid addition salts of the compounds of the formula (I) of the invention include in particular salts with pharmaceutically acceptable inorganic or organic acids. Preferred are pharmaceutically acceptable acid addition salts. Inorganic and organic acids that are able to form acid addition salts, including pharmaceutically acceptable salts with the compounds having basic nitrogen atom and methods of their preparation are well known in the art. Salts with inorganic acids may in particular comprise salts of hydrochloric, hydrobromic, sulphuric and phosphoric acids. Salts with organic acids may in particular comprise salts of methanesulphonic, ethanesulphonic, p-toluenesulphonic, benzenesulphonic, naphthalenesulphonic, acetic, propionic, lactic, tartaric, malic, citric, fumaric, maleic, and benzoic acids. It should be understood that the scope of the invention includes also salts with acids other than pharmaceutically acceptable ones that can be used especially as intermediates in the preparation, isolation and purification of the compounds of the invention.

Specific compounds of the invention are selected from the group consisting of the compounds presented below in the Examples and their acid addition salts, especially pharmaceutically acceptable acid addition salts, including inorganic and organic acids addition salts.

The compounds of formula (I) can be prepared in a manner described below generally and specifically in the examples of preparation of Intermediates and Compounds of the invention, and outlined in Schemes 1, 2 and 3.

Scheme 1
when R³ = H or alkyl
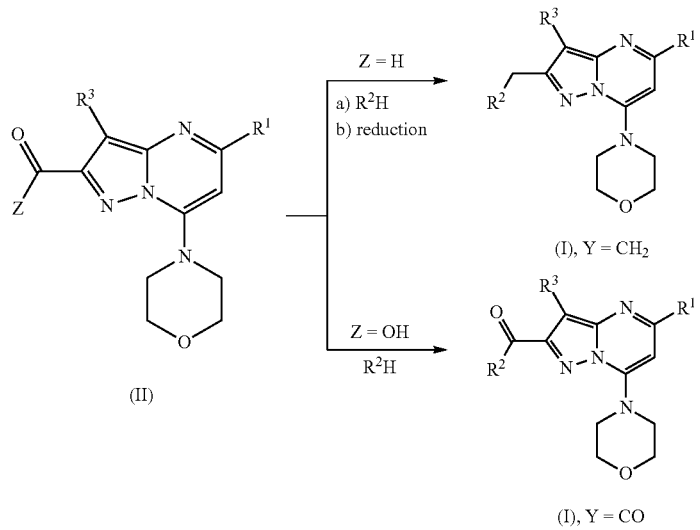
when R³ = halogen
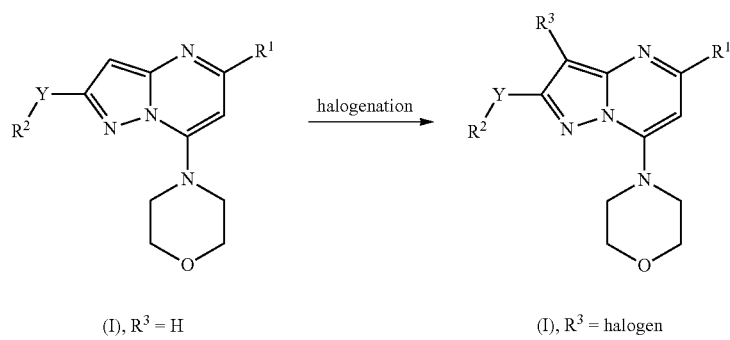
Scheme 2
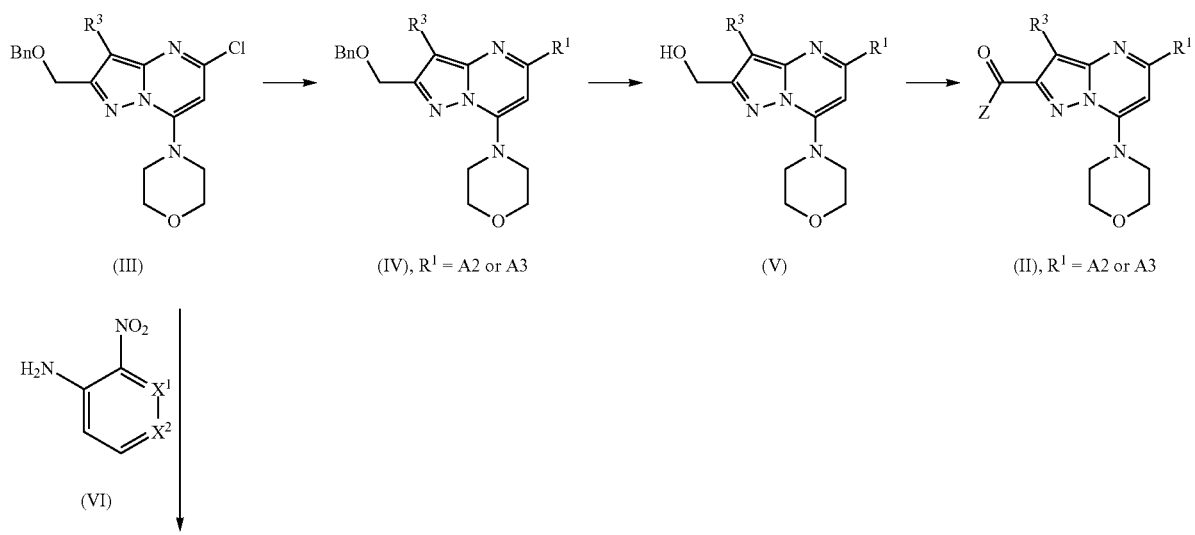

-continued
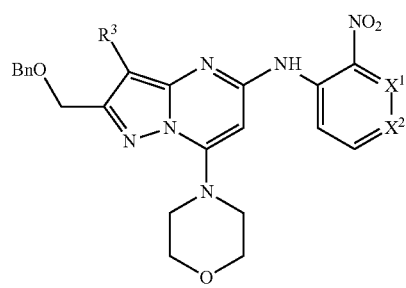
(VII), R¹ = A1
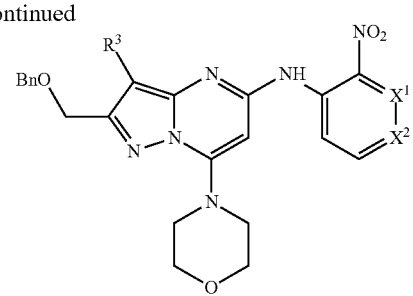
(VIII)
R⁴COOH →
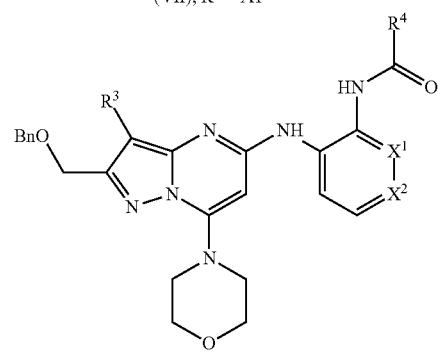
(IX)
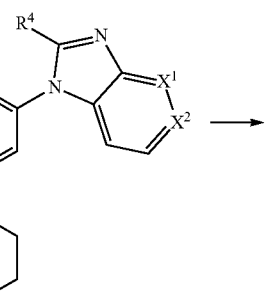
(X)
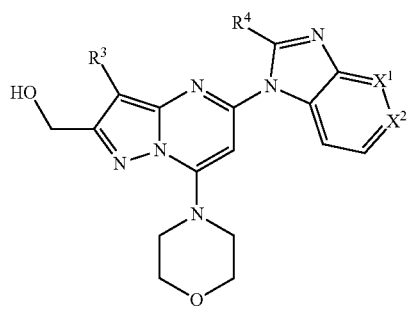
(XI)
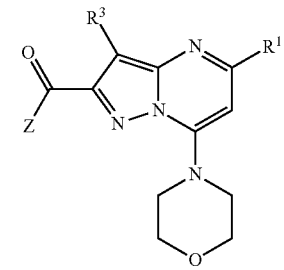
(II), R¹ = A1
Scheme 3
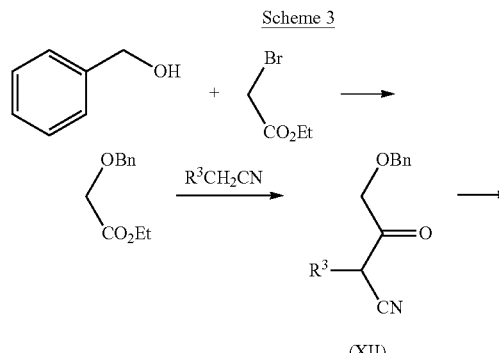
(XII)
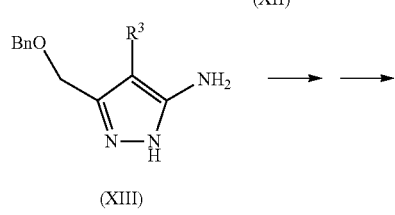
(XIII)
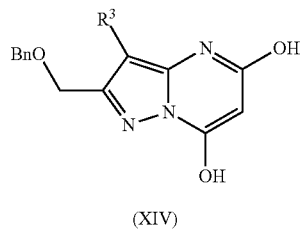
(XIV)
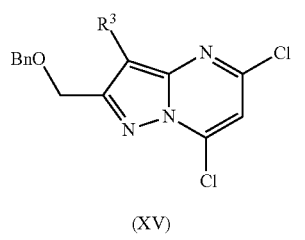
(XV)

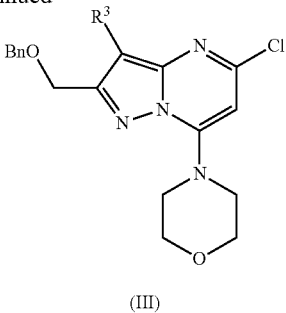

(III)

As shown in the above Scheme 1, the compounds of formula (I) wherein $R^3$ represents hydrogen atom or C1-C4 alkyl, and further symbols have the meaning as defined above, can be obtained from an aldehyde or acid of the formula (II) wherein Z represents hydrogen atom or OH, respectively, and further symbols have the meaning as defined for formula (I).

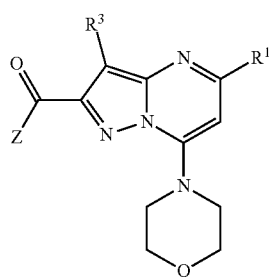

(II)

The compound of the formula (II) wherein Z represents hydrogen atom is reacted with amine of the formula $R^2H$ in the reductive amination reaction to obtain the compound of the formula (I) wherein Y represents $CH_2$ and $R^3$ represents hydrogen atom or C1-C4 alkyl.

The reaction of reductive amination with amine $R^2H$ can be carried out in the temperature range from 0° C. to the boiling point of the lowest boiling component of the reaction mixture, in an organic solvent such as for example chloroform, dichloromethane, dioxane, dimethylformamide, dimethylacetamide, toluene, hexane, tetrahydrofuran, or dimethoxyethane. Reducing agent can be, for example, sodium borohydride, sodium triacetoxyborohydride, or sodium cyanohydride. Most suitable conditions are the use of dichloromethane as the solvent, sodium triacetoxyborohydride as the reducing agent, and carrying out the reaction at room temperature.

The compound of the formula (II) wherein Z represents OH is reacted with amine of the formula $R^2H$ in the amidation reaction to obtain the compound of the formula (I) wherein Y represents >C=O and $R^3$ represents hydrogen atom or C1-C4 alkyl.

The amidation reaction with amine $R^2H$ can be carried out in the temperature range from 0° C. to the boiling point of the lowest boiling component of the reaction mixture (reflux temperature), in an organic solvent such as, for example, chloroform, dichloromethane, dioxane, dimethylformamide, dimethylacetamide, toluene, hexane, tetrahydrofuran, dimethoxyethane, dimethylsulphoxide, ethyl acetate, acetonitrile or diethyl ether. The reaction is carried out in the presence of carbodiimide, for example N,N'-diisopropylcarbodiimide, N,N'-dicyclohexylcarbodiimide, 1-ethyl-3-(3-dimethylaminopropyl)carbodiimide chlorhydrate or 1-[bis(dimethylamino)methylene]-1H-1,2,3-triazolo[4,5-b]pyridinium 3-oxide hexafluorophosphate (HATU), an additive such as 1-hydroxybenzotriazole (HOBt) or N-hydroxysuccinimide, and tertiary amine such as, for example, triethylamine (TEA) or N,N-diisopropylethylamine (DIPEA). The most suitable conditions for carrying out amidation are room temperature in dimethylformamide, in the presence of 1-ethyl-3-(3-dimethylaminopropyl)carbodiimide (EDCI) hydrochloride, 1-hydroxybenzotriazole (HOBt) additive and triethylamine (TEA).

The compounds of formula (I) wherein $R^3$ represents halogen atom can be prepared by halogenation of the compounds of the formula (I) wherein $R^3$ represents hydrogen atom.

Halogenation reaction can be carried out using molecular halogen or N-halosuccinimide as a halogenating agent at the temperature in the range 0° C. to the boiling point of the lowest boiling component of the mixture, in an organic solvent such as, for example, chloroform, dichloromethane, dioxane, dimethylformamide, dimethylacetamide, toluene, hexane, tetrahydrofuran, dimethoxyethane, dimethylsulphoxide, ethyl acetate, acetonitrile, or diethyl ether. The most suitable conditions for carrying out this reaction are the use of N-halosuccinimide in dichloromethane as a solvent, at 30° C.

The compounds of formula (II) are prepared from the compounds of the formula (III), wherein $R^3$ represents hydrogen atom or C1-C4 alkyl, and Bn represents benzyl,

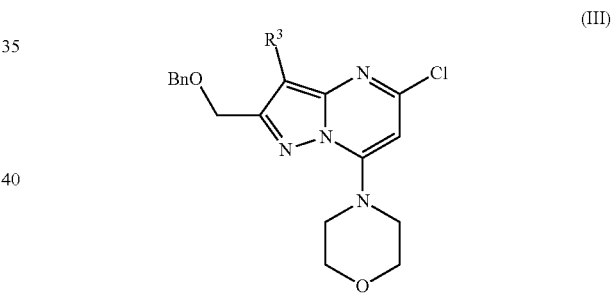

(III)

as outlined in Scheme 2.

In the case of preparation of the compound of the formula (II), wherein $R^1$ represents A2 or A3, the compound of the formula (III) is subjected to Suzuki reaction with boronic acid $R^1B(OH)_2$ or its ester, especially cyclic ester, such as pinacol ester, to obtain the compound of the formula (IV), wherein Bn is benzyl protecting group.

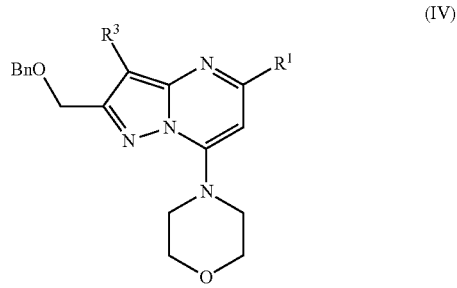

(IV)

In Suzuki reaction there are used palladium catalysts, for example palladium acetate, tetrakis(tri phenyl phosphino) palladium(0), bis(triphenylphosphino)-palladium chloride, tris(dibenzylideneacetone)dipalladium(0), 1,1'-bis(diphenyl-phosphino)ferrocenepalladium(II) dichloride dichloromethane adduct, a base, for example sodium phosphate, sodium carbonate, potassium carbonate, cesium carbonate, or sodium acetate, and an organic solvent, for example toluene, hexane, tetrahydrofuran, dioxane, or 1,2-dimethoxyethane, at the temperature from the range 0° C. to the boiling point of the lowest boiling component of the mixture. The most suitable conditions of carrying out the reaction are tetrakis-(triphenylphosphino)palladium(0) as a catalyst, 2M aqueous sodium carbonate solution as a base, and 1,2-dimethoxyethane as a solvent at reflux temperature.

Subsequently, the compound of the formula (IV) is deprotected by removing benzyl group (Bn) protecting hydroxyl group to obtain a compound of the formula (V).

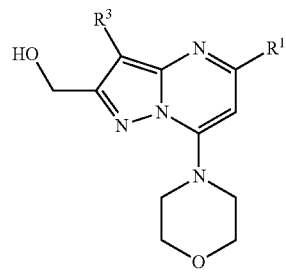

(V)

Removal of benzyl protecting group can be carried out by hydrogenation of the compound of the formula (IV) in the presence of palladium on active carbon, in an organic solvent such as, for example, methanol, ethanol, dimethylformamide, dioxane, cyclohexane, toluene, or their mixtures, at the temperature from 0° C. to the boiling point of the lowest boiling component of the mixture, under hydrogen pressure in the range from 1 to 100 bar. The most suitable conditions of carrying out the reaction are dimethylformamide (DMF) and ethanol (EtOH) solvent mixture with the addition of formic acid, at elevated temperature, such about 60° C., under hydrogen pressure of about 1 bar.

The compound of the formula (V) thus obtained is converted into aldehyde or acid of the formula (II) by oxidation, using suitable oxidizing agents.

Compound of the formula (V) can be converted into aldehyde of the formula (II) by oxidation with Collins reagent, Dess-Martin reagent, pyridinium dichromate (PDC), pyridinium chlorochromate (PCC), 2-iodoxybenzoic acid (IBX), manganese dioxide or in the Swern reaction, in a solvent such as dichloromethane, acetonitrile, hexane, toluene, dimethylformamide (DMF), dimethylacetamide, dimethylsulphoxide (DMSO), or dioxane, at the temperature from 0° C. to the boiling point of the lowest boiling component of the mixture. The most suitable conditions of carrying out the reaction are the use of Dess-Martina reagent in a solvent such as DMF, at room temperature.

The compound of the formula (V) can be converted into acid of the formula (II) by oxidation with Jones reagent, potassium permanganate, pyridinium dichromate (PDC), ruthenium tetraoxide, 2,2,6,6-tetramethylpiperidinium N-oxide, in a solvent such as acetonitrile, water, toluene, acetone, dioxane, or tetrahydrofuran, at a temperature from 0° C. to the boiling point of the lowest boiling component of the mixture. The most suitable conditions are the use of Jones reagent in an aqueous solution at reflux temperature.

In the case of the preparation of the compound of the formula (II), wherein $R^1$ represents A1, the compound of the formula (III) is first converted in the Buchwald-Hartwig reaction with nitrocompound of the formula (VI):

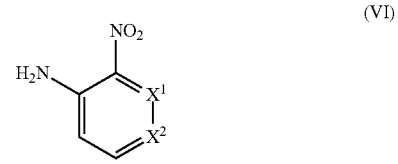

(VI)

into compound of the formula (VII)

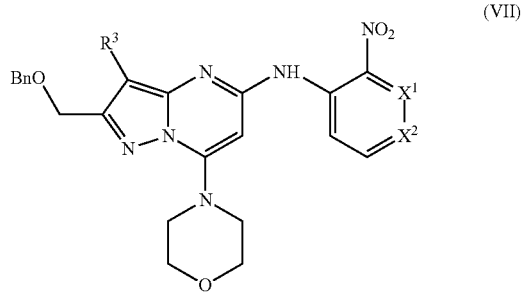

(VII)

wherein Bn represents benzyl protecting group.

Buchwald-Hartwig reaction is carried out in the presence of a palladium catalyst, for example palladium acetate, tetrakis(triphenylphosphino)palladium(0), bis(triphenylphosphino)palladium chloride, tris(di benzylideneacetone) dipalladium(0), 1,1'-bis(diphenylphosphino)ferrocenepalladium(II) dichloride dichloromethane adduct, a base, for example sodium phosphate, sodium carbonate, potassium carbonate, cesium carbonate, sodium acetate, sodium hydroxide, potassium hydroxide, sodium tert-butanolate, or potassium tert-butanolate, a phosphate ligand such as, for example, triphenylphosphine, 9,9-dimethyl-4,5-bis(diphenylphosphine)xanthene, (2-biphenyl)di-tert-butylphosphine, 2-dicyclohexylphosphine-2',4',6'-triisopropylbiphenyl, (2-biphenyl)dicyclohexylphosphine, and an organic solvent, for example toluene, hexane, tetrahydrofuran, dioxane, or 1,2-dimethoxyethane, at a temperature from 0° C. to the boiling point of the lowest boiling component of the mixture. The most suitable conditions of carrying out the reaction are reflux temperature in the presence of tris(dibenzylideneacetone)-dipalladium(0) as a catalyst, 9,9-dimethyl-4,5-bis(diphenylphosphine)xanthene, cesium carbonate, in toluene as a solvent.

Subsequently, the compound of the formula (VII) is reduced to obtain a compound of the formula (VIII)

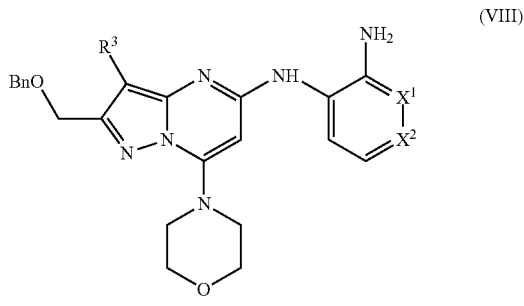

(VIII)

The compound of the formula (VIII) is then subjected to amidation reaction with an acid of the formula $R^4COOH$ in a manner analogous to that described for the preparation of the compound of the formula (I) from the compound of the formula (II) when Z is hydroxyl group (—OH), to obtain a compound of the formula (IX).

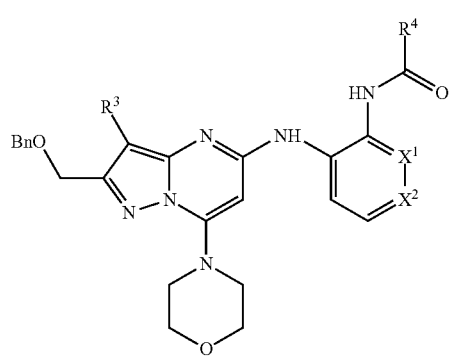

(IX)

The compound of the formula (IX) is converted to a compound of the formula (X) via cyclisation by heating at reflux in acetic acid.

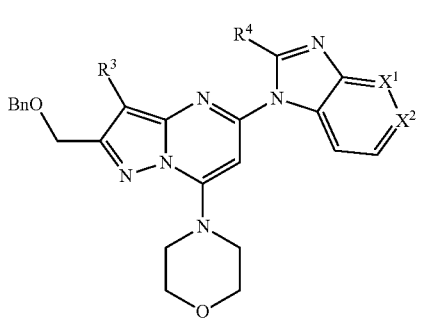

(X)

Subsequently, benzyl group protecting hydroxyl group is removed from the compound (X), in a manner such as described above for deprotection of hydroxyl group in the compound of the formula (IV), to obtain a compound of the formula (XI)

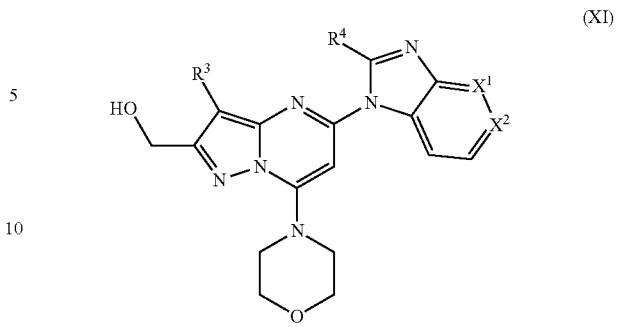

(XI)

and compound of the formula (XI) thus obtained is converted by oxidation into an aldehyde or acid of the formula (II), wherein $R^1$ represents A1 group, using suitable oxidizing agent, as described above for oxidation of the compound of the formula (V).

Compound of the formula (III) can be prepared as shown in Scheme 3.

Processes of the preparation of Intermediates presented in Scheme 3 were developed on the basis of literature methods for compounds of similar structure.

In accordance with Scheme 3, reaction of benzyl alcohol with ethyl bromoacetate in the presence of a strong base, such as sodium hydride, analogously as described in WO2011/109267, gives ethyl 2-benzyloxyacetate, which subsequently is converted into nitrile of the formula (XII) in the reaction with nitrile of the formula $R^3CH_2CN$, wherein $R^3$ represents hydrogen atom or C1-C4 alkyl, carried out in the presence of a strong base, such as butyllithium, analogously as described in WO2009/106539. Nitrile of the formula (XII) is converted into compound of the formula (XIII) in cyclization reaction with hydrazine, analogously as described in WO2009/106539. Compound of the formula (XIII), by cyclization reaction with diethyl malonate in the presence of a strong base, such as sodium ethanolate, is converted into compound of the formula (XIV), which is further converted into compound of the formula (XV) by chlorination with phosphoryl trichloride ($POCl_3$), and then the compound of the formula (XV) is converted into compound of the formula (III) by reaction with morpholine in the presence of a base, such as sodium carbonate. Conditions and a manner of carrying out reactions presented in Scheme 3 are described in details below in the description of preparing Intermediates.

Intermediates of the formula $R^2H$ are either known compounds that are commercially available or can be obtained using known methods, in a manner presented in details below in the description of preparing Intermediates. In most cases, reductive amination reaction described above between a compound including carbonyl system and an appropriate amine was employed for preparing Intermediates $R^2H$. For compounds $R^2H$ comprising urea system, a reaction between primary amine and isocyanate derivative was employed. The reaction can be carried out at a temperature from −80° C. to the boiling temperature of the lowest boiling component of the mixture, in an organic solvent, such as for example chloroform, dichloromethane, dioxane, dimethylformamide, dimethylacetamide, toluene, hexane, tetrahydrofuran, dimethoxyethane, dimethylsulphoxide, acetonitrile, or diethyl ether.

Boronic acids $R^1B(OH)_2$ and their esters, such as pinacol esters, are commercially available or can be obtained using Miyaura reaction or in the reaction between haloderivative and boronic acid or its ester in the presence of a base or palladium catalyst.

Nitriles of the formula $R^3CH_2CN$, wherein $R^3$ represents hydrogen atom or C1-C4 alkyl, are known compounds that are commercially available.

The compounds of the formula (I) can be administered in the treatment of diseases and disorders mentioned herein as chemical compound or in the form of pharmaceutical composition or pharmaceutical formulation containing them. Typically, they will be used as pharmaceutical composition or pharmaceutical formulation containing the compound of the invention or its pharmaceutically acceptable salt, in combination with pharmaceutically acceptable carriers and auxiliary substances.

In the treatment of disorders, diseases, and conditions mentioned above the pharmaceutical composition of the invention can be administered by any suitable route, preferably oral, parenteral or inhalation route and will be in the form of a preparation destined for use in medicine, depending on the intended administration route.

Compositions for oral administration can have the form of solid or liquid preparations. Solid preparations can have, for example, the form of a tablet or capsule produced in a conventional manner from pharmaceutically acceptable inactive excipients such as binders (for example, pregelatinised corn starch, polyvinylpyrrolidone or hydroxypropylmethylcellulose); fillers (for example lactose, saccharose, carboxymethylcellulose, microcrystalline cellulose or calcium hydrogenphosphate); disintegrants (for example crosspovidone, corn starch or sodium starch glycolate); lubricants (for example magnesium stearate, talc or silica), wetting agents (for example sodium laurylsulphate). Tablets can be coated with coatings well known in the art, such as simple coatings, delayed/controlled-release coatings or enteric coatings. Liquid preparations for oral administration can be in the form of, for example, solutions, syrups or suspensions, or can have the form of dry solid product for reconstitution in water or other suitable vehiculum before use. Such liquid preparations can be prepared using conventional means from pharmaceutically acceptable inactive excipients, such as suspending agents (for example sorbitol syrup, cellulose derivatives or hydrogenated edible oils), emulsifiers (for example lecithine or acacia gum), nonaqueous vehicles (for example mandelic oil, oil esters, ethyl alcohol or fractionated vegetable oils), and preservatives (for example methyl or propyl p-hydroxybenzoate or sorbic acid). Preparations can also include suitable buffering agents, flavoring agents, coloring agents and sweeteners.

Preparations for oral administration can be formulated so as to obtain controlled release of the active compound using methods known for a person skilled in the art.

Parenteral route of administration includes administration by intramuscular and intravenous injections, as well as intravenous infusions. Compositions for parenteral administration can, for example, have the form of a unit dosage form, such as ampoules, or multi-dosage containers, with the addition of a preservative. Compositions can have the form such as suspension, solution or emulsion in an oily or aqueous vehiculum, and can include excipients such as suspending agents, stabilizers, and/or dispersing agents. Alternatively, the active ingredient can be formulated as a powder for reconstitution before use in a suitable carrier, for example sterile, pyrogen-free water.

Compositions for administration via inhalation route can have the inhalation form and administered by nebulization. Such preparations include an active compound and auxiliary substance(s) administered as an aerosol, i.e. a system of finely divided small particles of solid or liquid substance suspended in a gas. Auxiliary substances used in nebulization can be for example sodium chloride as an isotonicity agent, inorganic acids and hydroxides as pH regulators and stabilizers, benzalkonium chloride as a preservative, sodium citrate as a buffering agent, polysorbate 80 as a surfactant, ethanol and propylene glycol as a co-solvent, and sulphates (VI) as anti-oxidants. Preparations for administration by inhalation route can have the form of pressure inhalers or dry powder inhalers.

The method of treatment with the use of the compounds of the present invention will comprise administration of a therapeutically effective amount of the compound of the invention, preferably in the form of a pharmaceutical composition, to the subject in need of such treatment.

Proposed dosage of the compounds of the invention is from 0.1 to about 1000 mg per day, in a single dose or in divided doses. It will be apparent for a person skilled in the art that selection of a dosage required for obtaining desirable biological effect will depend on many factors, for example specific compound, the indication, the manner of administration, the age and condition of a patient and that exact dosage will be ultimately determined by a responsible physician.

EXAMPLES

Preparation of Intermediates

Ethyl 2-benzyloxyacetate

To the suspension of 21.8 g (0.545 mol) of 60% NaH in 1000 ml of dry toluene 47 ml (0.454 mol) of benzyl alcohol were added dropwise during 30 minutes. The whole mixture was stirred at room temperature for 4 h. The suspension was cooled in a water-ice bath and 66 ml (0.595 mol) of ethyl bromoacetate were added dropwise during 45 minutes. The reaction mixture was heated to room temperature and stirred for 1 h. The whole mixture was poured onto ice water (1200 ml) acidified with 10 ml of concentrated hydrochloric acid. Phases were separated and aqueous phase was extracted with 3× diethyl ether. Combined organic phases were washed with brine and dried over anhydrous magnesium sulphate. After filtration of the drying agent, organic solvents were evaporated under reduced pressure. The residue was separated by distillation under reduced pressure. After distillation, 66.7 g (76%) of ethyl 2-benzyloxyacetate were obtained as a colorless liquid ($T_b$=104-106° C./0.7 tor). $^1$H NMR (500 MHz, CDCl$_3$) δ: 7.39-7.28 (m; 5H), 4.63 (s; 2H), 4.23 (q; J=7.1 Hz; 2H), 4.09 (s; 2H), 1.28 (t; J=7.1 Hz; 3H). MS-ESI: (m/z) calculated for $C_{11}H_{14}O_3$ [M+H]$^+$: 195.23; determined 195.1.

Intermediate XII-1: 4-benzyloxy-3-oxobutyronitrile

To the argonated flask filled with 750 ml of dry THF cooled to −78° C., 200 ml (0.5 mol) of 2.5 M n-BuLi hexane solution were added, and then 28 ml (0.533 mol) of acetonitrile were added dropwise. The whole mixture was stirred at −78° C. for 2 h. To the suspension 77.7 g (0.4 mol) of ethyl 2-benzyloxyacetate obtained above were added dropwise and stirring was continued at −78° C. for 1 h. The reaction was quenched by adding saturated ammonium chloride solution. The mixture was poured onto ice-water and acidified with 6 M hydrochloric acid. Aqueous phase was extracted with diethyl ether. Combined organic phases were washed with brine and dried over anhydrous magnesium sulphate. Drying agent was filtered off and the solvent was evaporated under reduced pressure. Intermediate XII-1 was used in the next step without purification. MS-ESI: (m/z) calculated for $C_{11}H_{11}NO_2$ [M+H]$^+$: 190.22; determined 190.1.

Intermediate XII-2: 4-benzyloxy-2-methyl-3-oxobutylonitrile

Obtained from ethyl 2-benzyloxyacetate and propionitrile, analogously as for Intermediate XII-1.

Intermediate XIII-1: 3-(benzyloxymethyl)-1H-pyrazol-5-amine

To Intermediate XII-1 (about 75.7 g, 0.4 mol) obtained above 500 ml of ethanol and 100 ml (2.1 mol) of hydrazine monohydrate were added. The mixture was refluxed for 16 h. After evaporation of the solvent to dryness under reduced pressure, the residue was added with chloroform and dried over anhydrous sodium sulphate. Drying agent was filtered off and the solvent was evaporated, and the mixture was separated on a chromatographic column using ethyl acetate/methanol from 100/0 to 95/5 as an eluent. After separation, 70.4 g (87%) of Intermediate XIII-1 were obtained as a brown oil. $^1$H NMR (300 MHz; CDCl$_3$) δ: 7.39-7.28 (m; 5H); 5.59 (s; 1H); 4.53 (s; 2H); 4.50 (s; 2H). MS-ESI: (m/z) calculated for $C_{11}H_{13}N_3O$ [M+H]$^+$: 204.25; determined 204.1.

Intermediate XIII-2: 3-(benzyloxymethyl)-4-methyl-1H-pyrazol-5-amine

Obtained from Intermediate_XII-2, analogously as described for Intermediate XIII-1.

Intermediate XIV-1: 2-(benzyloxymethyl)pyrazolo[1,5-a]pyrimidin-5,7-diol

To the flask with sodium ethanolate solution obtained from 53 g (0.74 mol) sodium ethanolate and 700 ml of ethanol 70.4 g (0.35 mol) of Intermediate XIII-1 dissolved in 200 ml of ethanol and 80 ml (0.53 mol) of diethyl malonate were added. The reaction was carried out at reflux for 24 h. The reaction mixture was cooled to room temperature, then the solvent was evaporated under reduced pressure. The residue was dissolved in 1200 ml of water and acidified with concentrated hydrochloric acid to pH about 2. Creamy solid precipitated from the solution was filtered off, washed and dried. 79 g (84%) of Intermediate XIV-1 were obtained as a creamy solid. MS-ESI: (m/z) calculated for $C_{14}H_{13}N_3O_3$ [M+Na]$^+$: 294.26; determined 294.1.

Intermediate XIV-2: 2-(benzyloxymethyl)-3-methyl-pyrazolo[1,5-a]pyrimidin-5,7-diol Obtained from Intermediate XIII-2, analogously as for Intermediate_XIV-1.

Intermediate XV-1: 2-(benzyloxymethyl)-5,7-dichloropyrazolo[1,5-a]pyrimidine

The suspension of 30 g (0.11 mol) of Intermediate XIV-1 in 270 ml of acetonitrile was cooled in a water-ice bath and 206 ml (2.2 mol) of POCl$_3$ were added. The reaction was carried out at 80° C. for 5 h. The reaction mixture was concentrated on evaporator to remove acetonitrile and POCl$_3$. The residue was poured onto water with ice, and alkalized to pH 5 with saturated sodium hydrogencarbonate solution. Aqueous phase was extracted with ethyl acetate, and after separation the organic phase was dried over anhydrous sodium sulphate. After filtration of the drying agent and evaporation of the solvent, the residue was purified by column chromatography using heptane/ethyl acetate from 100/0 to 80/20 as an eluent. After separation 13 g (38%) of Intermediate XV-1 were obtained as a slightly yellow oil. $^1$H NMR (300 MHz, CDCl$_3$) δ: 7.41-7.27 (m; 5H); 6.96 (s; 1H); 6.80 (s; 1H); 4.81 (s; 2H); 4.65 (s; 2H). MS-ESI: (m/z) calculated for $C_{14}H_{11}Cl_2N_3O$ [M+H]$^+$: 309.17; determined 308.0.

Intermediate XV-2: 2-(benzyloxymethyl)-5,7-dichloro-3-methylpyrazolo[1,5-a]-pyrimidine Obtained from Intermediate XIV-2, analogously to the procedure described for Intermediate XV-1.

Intermediate III-1: 2-(benzyloxymethyl)-5-chloro-7-(morpholin-4-yl)pyrazolo[1,5-a]pyrimidine To the solution of 13 g (42.3 mmol) of Intermediate XV-1 dissolved in 450 ml of acetone 5.38 g (50.8 mmol) of sodium carbonate and 6.65 ml (76.2 mmol) of morpholine were added. The reaction was carried out at room temperature for 1.5 h. 500 ml of water were added to the reaction mixture, and precipitated white solid was filtered off. The solid was washed with water and 200 ml of water/acetone mixture (2/1), then dried. 14 g (92%) of Intermediate III-1 were obtained as a white solid. $^1$H NMR (300 MHz, CDCl$_3$) δ: 7.41-7.27 (m; 5H); 6.56 (s; 1H); 6.06 (s; 1H); 4.73 (s; 2H); 4.62 (s; 2H); 3.98-3.90 (m; 4H); 3.82-3.74 (m; 4H). MS-ESI: (m/z) calculated for $C_{18}H_{19}ClN_4O_2$ [M+H]$^+$: 359.83; determined 359.2.

Intermediate III-2: 2-(benzyloxymethyl)-5-chloro-3-methyl-7-(morpholin-4-yl)-pyrazolo[1,5-a]pyrimidine Obtained from Intermediate XV-2, analogously to the procedure described for Intermediate III-1.

Intermediate IV-1: 2-(benzyloxymethyl)-5-(1H-indol-4-yl)-7-(morpholin-4-yl)-pyrazolo[1,5-a]pyrimidine

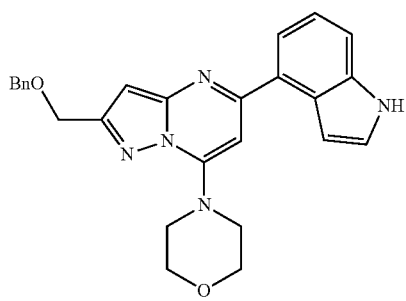 [SMILES: c1ccc(COCc2cc3nc(-c4cccc5[nH]ccc45)cc(N4CCOCC4)n3n2)cc1]

To the solution of 1.88 g (5.24 mmol) of Intermediate III-1 dissolved in 52 ml of 1,2-dimethoxyethane (DME) there were added 1.97 g (7.87 mmol) of indole-4-boronic acid pinacol ester, 0.61 g (0.52 mmol) of tetrakis(triphenylphosphino)-palladium (0) and 5.2 ml of 2M aqueous sodium carbonate solution. The reaction was carried out at reflux for 16 h. The reaction mixture was cooled to room temperature, filtered over Celit®, and solid washed with ethyl acetate. The filtrate was concentrated using evaporator. The residue was separated by column chromatography, using heptane/ethyl acetate 100/0 to 30/70 as an eluent to obtain 1.91 g (83%) of Intermediate IV-1. $^1$H NMR (300 MHz, CDCl$_3$) δ: 8.61 (bs; 1H); 7.61 (dd; J=7.4; 0.8 Hz; 1H); 7.50-7.23 (m; 8H); 7.13-7.07 (m; 1H); 6.74 (s; 1H); 6.66 (s; 1H); 4.81 (s; 2H); 4.67 (s; 2H); 4.02-3.95 (m; 4H); 3.81-3.73 (m; 4H). MS-ESI: (m/z) calculated for C$_{11}$H$_{13}$N$_3$O [M+H]$^+$: 204.25; determined 204.1.

Intermediates od IV-2 to IV-9, presented in Table 1 were obtained by proceeding in an analogous manner as described for preparation of Intermediate IV-1 and starting from Intermediate III-1 (R$^3$=H) or III-2 (R$^3$=Me) and pinacol ester of respective boronic acid R$^1$B(OH)$_2$.

TABLE 1

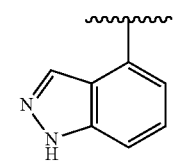

(R$^3$ = H, alkyl)

| Nr | R$^1$ | R$^3$ | MS-ESI [M + H]$^+$ |
|---|---|---|---|
| IV-2 | 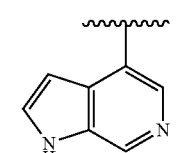 | H | 458.2 |
| IV-3 | 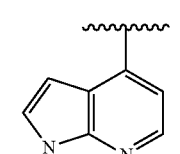 | H | 441.2 |
| IV-4 | 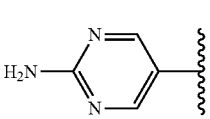 | H | 441.2 |
| IV-5 | 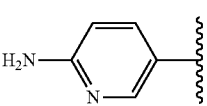 | H | 441.2 |
| IV-6 | 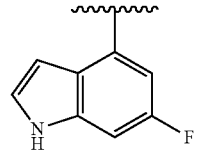 | H | 418.2 |

TABLE 1-continued

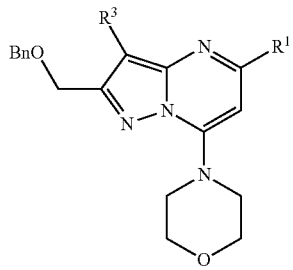

(R$^3$ = H, alkyl)

| Nr | R$^1$ | R$^3$ | MS-ESI [M + H]$^+$ |
|---|---|---|---|
| IV-7 | 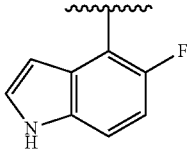 [SMILES: *c1c(F)ccc2[nH]ccc12] | H | 417.2 |
| IV-8 | 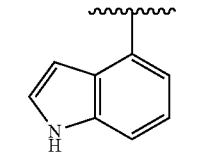 [SMILES: *c1cccc2[nH]ccc12] | H | 458.2 |
| IV-9 | 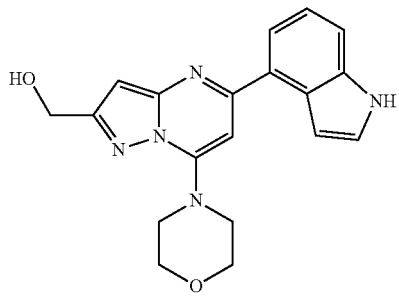 | Me | 454.2 |

Intermediate V-1: [7-(morpholin-4-yl)-5-(1H-indol-4-yl)pyrazolo[1,5-a]pyrimidin-2-yl]methanol

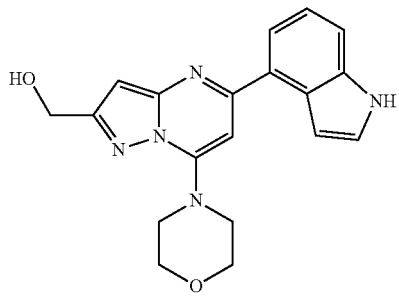 [SMILES: OCc1cc2nc(-c3cccc4[nH]ccc34)cc(N3CCOCC3)n2n1]

To the solution of 5.0 g (9.1 mmol) of Intermediate IV-1 in 120 ml of DMF and 60 ml of EtOH 11.3 g of 10% Pd/C and 100 μl of formic acid were added. The reaction was carried out at 60° C. under hydrogen pressure for 24 h. After cooling the reaction mixture to room temperature the catalyst was filtered-off on a Celite®, the solid was washed with EtOH, and the filtrate was then concentrated using evaporator. The mixture obtained was purified by column chromatography, using heptane/ethyl acetate from 100/0 to 0/100 as the eluent. 2.08 g (66%) of Intermediate V-1 were obtained after resolution. $^1$H NMR (300 MHz, DMSO) δ 11.36 (bs; 1H); 7.70-7.63 (m; 1H); 7.59-7.52 (m; 1H);

7.52-7.46 (m; 1H); 7.28-7.20 (m; 1H); 7.14-7.09 (m; 1H); 6.78 (s; 1H); 6.55 (s; 1H); 5.36 (t; J=6.0 Hz; 1H); 4.66 (d; J=6.0 Hz; 2H); 3.90-3.83 (m; 4H); 3.83-3.75 (m; 4H). MS-ESI: (m/z) calculated for $C_{19}H_{19}N_5O_2$ [M+H]$^+$: 350.39; determined 350.2.

Intermediates V-2 to V-9 presented in Table 2 were obtained starting from respective Intermediate IV in an analogous manner as described for preparation of Intermediate V-1.

TABLE 2

V (structure with $R^3$, HO-, $R^1$, morpholine substituents on pyrazolo[1,5-a]pyrimidine)

($R^3$ = H, alkyl)

| Nr | $R^1$ | $R^3$ | MS-ESI [M + H]$^+$ |
|---|---|---|---|
| V-2 | 4-(5-fluoro-1H-indol-4-yl) | H | 368.2 |
| V-3 | 1H-indazol-4-yl | H | 351.2 |
| V-4 | 1H-pyrrolo[2,3-c]pyridin-4-yl | H | 351.2 |
| V-5 | 1H-pyrrolo[2,3-b]pyridin-4-yl | H | 351.2 |
| V-6 | 2-aminopyrimidin-5-yl | H | 328.2 |
| V-7 | 6-aminopyridin-3-yl | H | 327.1 |
| V-8 | 6-fluoro-1H-indol-4-yl | H | 368.2 |
| V-9 | 1H-indol-4-yl | Me | 364.2 |

Intermediate VII-1: 2-((benzyloxy)methyl)-7-(morpholin-4-yl)-N-(2-nitrophenyl)-pyrazolo[1,5-a]pyrimidine-5-amine

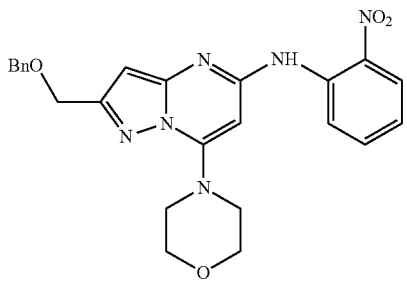

VII-1

1.65 g (4.6 mmol) of Intermediate III-1, 0.953 g (6.9 mmol) of 2-nitroaniline, 4.49 g (13.8 mmol) of cesium carbonate, 0.211 g (0.23 mmol) of tris(dibenzylide-neacetone)dipalladium(0), 0.266 g (0.46 mmol) of 9,9-dimethyl-4,5-bis(diphenyl-phosphine)xanthene and 46 ml of dry toluene were introduced to the reaction vessel. The whole mixture was argonated and stirred at 110° C. for 24 h. After cooling to room temperature, the reaction mixture was filtered through Celite® and the solid washed with ethyl acetate. The filtrate was concentrated using evaporator. The residue was resolved on a chromatographic column using heptane/ethyl acetate system from 50/50 to 0/100 as an eluent. 1.84 g (87%) of Intermediate VII-1 were obtained after resolution. MS-ESI: (m/z) calculated for $C_{24}H_{24}N_6O_4$ [M+H]$^+$: 461.49; determined 461.5.

Intermediates VII-2 to VII-5 presented in Table 3 were prepared in a manner analogous to that described for the preparation of Intermediate VII-1, starting from Intermediate III-1 ($R^3$=H) or III-2 ($R^3$=alkyl) and suitable nitroamine derivative of the formula VI in place of 2-nitroaniline.

TABLE 3

VII

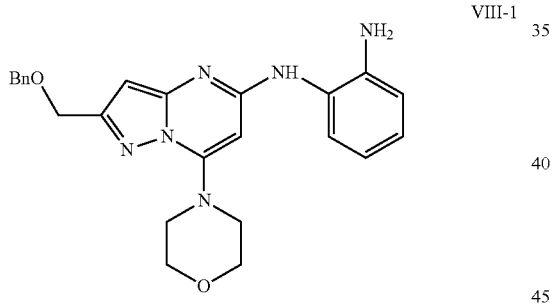

($R^3$ = H, alkyl)

| Intermediate | $R^3$ | $X^1$ | $X^2$ | MS-ESI [M + H]$^+$ |
|---|---|---|---|---|
| VII-2 | H | N | CH | 462.2 |
| VII-3 | H | CH | N | 462.2 |
| VII-4 | H | CH | C—OMe | 491.2 |
| VII-5 | Me | CH | CH | 475.2 |

Intermediate VIII-1: N-(2-(benzyloxymethyl)-7-(morpholin-4-yl)pyrazolo[1,5-a]-pyrimidin-5-yl)benzene-1,2-diamine

VIII-1

A mixture of 1.75 g (3.8 mmol) of Intermediate VII-1 and 3.94 g (19.0 mmol) of tin dichloride dihydrate (II) in ethanol (25 ml) was heated at reflux with stirring for about 20 h. After cooling the reaction to room temperature, 100 ml of ethyl acetate and 100 ml of saturated sodium hydrogencarbonate solution were added. The suspension was filtered through Celite® and phases were separated. The aqueous phase was extracted twice with ethyl acetate. Combined organic phases were dried over anhydrous sodium sulphate. Drying agent was filtered off and the solution was concentrated using evaporator. The mixture was resolved with chromatographic column (modified silicagel with propylamine), using the system heptane/ethyl acetate from 100/0 to 50/50 as an eluent. After resolution, 1.30 g (79%) of Intermediate VIII-1 were obtained. $^1$H NMR (300 MHz, CDCl$_3$) δ 7.41-7.27 (m; 5H); 7.3-7.17 (m; 1H); 7.17-7.08 (m; 1H); 6.87-6.75 (m; 2H); 6.17 (s; 1H); 5.34 (s; 1H); 4.68 (s; 2H); 4.61 (s; 2H); 3.93-3.86 (m; 4H); 3.57-3.49 (m; 4H). MS-ESI: (m/z) calculated for C$_{24}$H$_{26}$N$_6$O$_2$ [M+H]$^+$: 431.22; determined 431.2.

Intermediates VIII-2 to VIII-5 ($R^3$=H, alkyl) presented in Table 4 were obtained starting from suitable Intermediate VII analogously as described for the preparation of Intermediate VIII-1.

TABLE 4

VIII

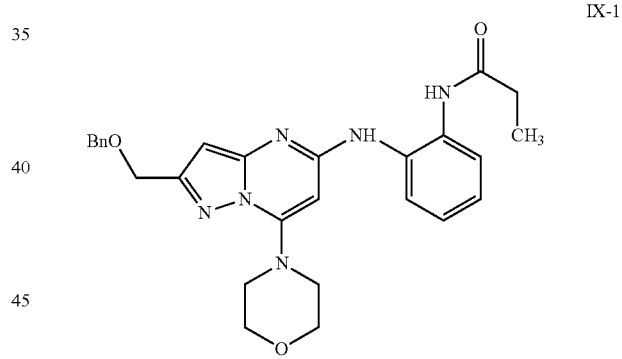

($R^3$ = H, alkyl)

| Intermediate | $R^3$ | $X^1$ | $X^2$ | MS-ESI [M + H]$^+$ |
|---|---|---|---|---|
| VIII-2 | H | N | CH | 432.2 |
| VIII-3 | H | CH | N | 432.2 |
| VIII-4 | H | CH | C—OMe | 461.2 |
| VIII-5 | Me | CH | CH | 445.2 |

Intermediate IX-1: N-(2-((2-(benzyloxymethyl)-7-(morpholin-4-yl)pyrazolo[1,5-a]-pyrimidin-5-yl)amino)phenyl)propionamide

IX-1

To the solution of 0.943 g (2.2 mmol) of Intermediate VIII-1 dissolved in 50.0 ml of dry DCM, 0.364 ml (0.36 g, 4.8 mmol) of propionic acid, 0.652 g (4.8 mmol) of HOBt, 0.920 g (4.8 mmol) of EDCI, and 0.916 ml (0.666 g, 6.6 mmol) of TEA were added. The whole mixture was stirred at room temperature for 48 h. 100 ml of water was added to the mixture and phases were separated. Aqueous phase was extracted 3× with DCM. Combined organic phases were dried over anhydrous sodium sulphate. After drying agent was filtered off and the solvent evaporated, the reaction mixture was separated on a chromatographic column, using heptane/ethyl acetate from 50/50 to 0/100 as an eluent. After separation 0.84 g (79%) of Intermediate IX-1 were obtained. $^1$H NMR (300 MHz, CDCl$_3$) δ 8.43 (s; 1H); 7.61-7.55 (m; 1H); 7.40-7.28 (m; 6H); 7.17-7.11 (m; 2H); 6.18 (s; 1H); 5.38 (s; 1H); 4.68 (s; 2H); 4.62 (s; 2H); 3.96-3.89 (m; 4H); 3.63-3.55 (m; 4H); 2.32 (q; J=7.6 Hz; 2H); 1.15 (t; J=7.6 Hz; 3H). MS-ESI: (m/z) calculated for C$_{27}$H$_{30}$N$_6$O$_3$ [M+H]$^+$: 487.25; determined 487.3.

Intermediates IX-2 to IX-13 ($R^3$=H, alkyl) presented in Table 5 were prepared analogously as described for Intermediate IX-1, starting from suitable Intermediate VIII and an acid $R^4$COOH in place of propionic acid.

TABLE 5

IX ($R^3$ = H, alkyl)

| Intermediate | $R^3$ | $R^4$ | $X^1$ | $X^2$ | MS-ESI [M + H]$^+$ |
|---|---|---|---|---|---|
| IX-2 | H | Me | CH | CH | 473.2 |
| IX-3 | H | CHF$_2$ | CH | CH | 509.2 |
| IX-4 | H | i-Pr | CH | CH | 501.3 |
| IX-5 | H | cyclo-Pr | CH | CH | 499.2 |
| IX-6 | H | Et | N | CH | 488.2 |
| IX-7 | H | Et | CH | N | 488.2 |
| IX-8 | H | Et | CH | C—OMe | 517.3 |
| IX-9 | H | CHF$_2$ | N | CH | 510.2 |
| IX-10 | H | CHF$_2$ | CH | N | 510.2 |
| IX-11 | H | CHF$_2$ | CH | C—OMe | 539.2 |
| IX-12 | H | CH$_2$—O—CH$_3$ | CH | CH | 503.2 |
| IX-13 | Me | CHF$_2$ | CH | CH | 523.2 |

Intermediate X-1: 2-(benzyloxymethyl)-5-(2-ethyl-benzimidazol-1-yl)-7-(morpholin-4-yl)pyrazolo[1,5-a]pyrimidine

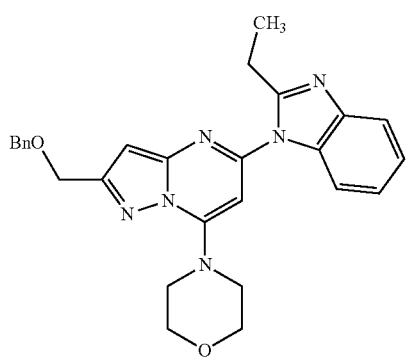

X-1

0.763 g (1.57 mmol) of Intermediate IX-1 were introduced to the flask and dissolved in 200 ml of ice acetic acid. The reaction was carried out at reflux for 24 h. After cooling the reaction mixture, the solution was concentrated using evaporator. The residue was diluted with water and then neutralized with saturated sodium hydrogencarbonate solution. Aqueous phase was extracted 3× with ethyl acetate. Combined organic fractions were dried over sodium sulphate. After drying agent was filtered off, the solvent was evaporated using evaporator. The reaction mixture was separated on a chromatographic column using heptane/ethyl acetate system from 100/0 to 0/100 as an eluent. After separation 0.459 g (62%) of Intermediate X-1 were obtained. $^1$H NMR (300 MHz, CDCl$_3$) δ 7.84-7.77 (m; 1H); 7.49-7.22 (m; 8H); 6.71 (s; 1H); 6.21 (s; 1H); 4.80 (s; 2H); 4.69 (s; 2H); 4.05-3.95 (m; 4H); 3.91-3.82 (m; 4H); 3.13 (q; J=7.5 Hz; 2H); 1.42 (t; J=7.5 Hz; 3H). MS-ESI: (m/z) calculated for C$_{27}$H$_{28}$N$_6$O$_2$ [M+H]$^+$: 469.23; determined 469.2.

Intermediates od X-2 to X-13 presented in Table 6 were prepared analogously as described for Intermediate, starting from suitable Intermediate IX analogously as described for the preparation of Intermediate X-1.

TABLE 6

X ($R^3$ = H, alkyl)

| Intermediate | $R^3$ | $R^4$ | $X^1$ | $X^2$ | MS-ESI [M + H]$^+$ |
|---|---|---|---|---|---|
| X-2 | H | Me | CH | CH | 455.2 |
| X-3 | H | CHF$_2$ | CH | CH | 491.2 |
| X-4 | H | i-Pr | CH | CH | 483.3 |
| X-5 | H | cyclo-Pr | CH | CH | 481.2 |
| X-6 | H | Et | N | CH | 470.2 |
| X-7 | H | Et | CH | N | 470.2 |
| X-8 | H | Et | CH | C—OMe | 499.2 |
| X-9 | H | CHF$_2$ | N | CH | 492.2 |
| X-10 | H | CHF$_2$ | CH | N | 492.2 |
| X-11 | H | CHF$_2$ | CH | C—OMe | 521.2 |
| X-12 | H | CH$_2$—O—CH$_3$ | CH | CH | 485.2 |
| X-13 | Me | CHF$_2$ | CH | CH | 505.2 |

Intermediate XI

Intermediates XI-1 to XI-13 presented in Table 7 were prepared analogously as described for Intermediate V-1, starting from suitable Intermediate X, and using ethyl acetate/ethanol 1/1 mixture in place of DMF and ethanol.

TABLE 7

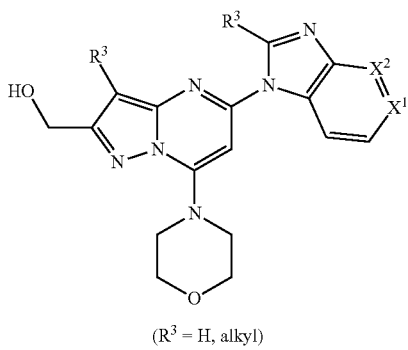

XI (R³ = H, alkyl)

| Intermediate | R³ | R⁴ | X¹ | X² | MS-ESI [M + H]⁺ |
|---|---|---|---|---|---|
| XI-1 | H | Et | CH | CH | 379.2 |
| XI-2 | H | Me | CH | CH | 365.2 |
| XI-3 | H | CHF₂ | CH | CH | 401.2 |
| XI-4 | H | i-Pr | CH | CH | 393.2 |
| XI-5 | H | cyclo-Pr | CH | CH | 391.2 |
| XI-6 | H | Et | N | CH | 380.2 |
| XI-7 | H | Et | CH | N | 380.2 |
| XI-8 | H | Et | CH | C—OMe | 409.2 |
| XI-9 | H | CHF₂ | N | CH | 402.1 |
| XI-10 | H | CHF₂ | CH | N | 402.1 |
| XI-11 | H | CHF₂ | CH | C—OMe | 431.2 |
| XI-12 | H | CH₂—O—CH₃ | CH | CH | 395.2 |
| XI-13 | Me | CHF₂ | CH | CH | 415.2 |

Intermediate II-1: 5-(1H-indol-4-yl)-7-(morpholin-4-yl)-pyrazolo[1,5-a]pyrimidin-2-carboxyaldehyde

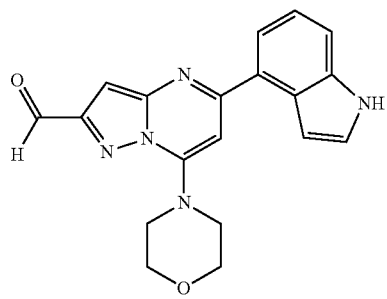 [SMILES: O=Cc1cc2nc(-c3cccc4[nH]ccc34)cc(N3CCOCC3)n2n1]

To the solution of 0.90 g (2.58 mmol) of Intermediate V-1 in 26 ml of dry DMF 1.31 g (3.09 mmol) of Dess-Martin reagent were added. The whole mixture was stirred at room temperature for 1 h. The solid was filtered-off and then washed with ethyl acetate. The obtained solution was concentrated under reduced pressure. The mixture was purified on a chromatographic column in a heptane/ethyl acetate from 100/0 to 30/70 system. After separation 0.70 g (78%) of Intermediate II-1 were obtained. ¹H NMR (300 MHz, CDCl₃) δ 10.22 (s; 1H); 8.47 (bs; 1H); 7.66-7.59 (m; 1H); 7.57-7.50 (m; 1H); 7.39-7.29 (m; 2H); 7.18-7.09 (m; 2H); 6.83 (s; 1H); 4.08-4.00 (m; 4H); 3.86-3.77 (m; 4H). MS-ESI: (m/z) calculated for C₁₉H₁₇N₅O₂ [M+H]⁺: 348.38; determined 348.1.

Intermediates od II-2 to II-9 presented in Table 8 were prepared starting from suitable Intermediate V, analogously as described for the preparation of Intermediate II-1.

TABLE 8

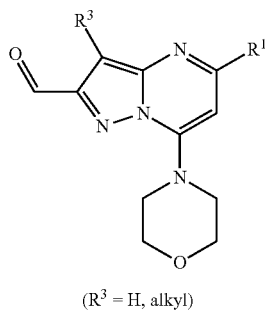

II (R³ = H, alkyl)

| Nr | R³ | R¹ | MS-ESI [M + H]⁺ |
|---|---|---|---|
| II-2 | H | 5-fluoro-1H-indol-4-yl | 366.1 |
| II-3 | H | 1H-indazol-4-yl | 349.1 |
| II-4 | H | 1H-pyrrolo[2,3-c]pyridin-4-yl | 349.1 |
| II-5 | H | 1H-pyrrolo[2,3-b]pyridin-4-yl | 349.1 |
| II-6 | H | 2-aminopyrimidin-5-yl | 326.1 |
| II-7 | H | 6-aminopyridin-3-yl | 325.1 |
| II-8 | H | 6-fluoro-1H-indol-4-yl | 366.1 |
| II-9 | Me | 1H-indol-4-yl | 362.2 |

Intermediate II-10: 5-(1H-indol-4-yl)-7-(morpholin-4-yl)-pyrazolo[1,5-a]-pyrimidin-2-carboxylic acid

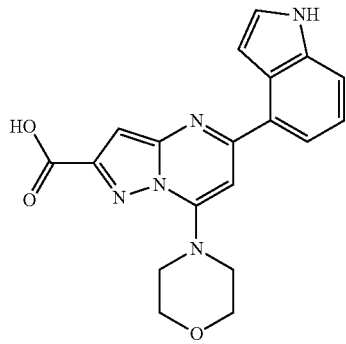

Obtained by oxidation of Intermediate II-1.

To the flask with 35 ml of 20% sulphuric acid solution 1.40 g (4.73 mmol) of potassium dichromate and then 1.1 g (3.15 mmol) of Intermediate II-1 were added. The whole mixture was brought to the reflux while stirring and maintained at that temperature for 5 h. The mixture was cooled to room temperature and the solid precipitated from the mixture was filtered-off. The solid was washed with water and then dried in the desiccator over $P_2O_5$. 0.56 g (49%) of raw Intermediate II-10 were obtained and used in a further step without purification.

Intermediates II-11 to 11-23 ($R^3$=H, alkyl) presented in Table 9 were prepared analogously as described for the preparation of Intermediate II-1, starting from suitable Intermediate XI.

TABLE 9

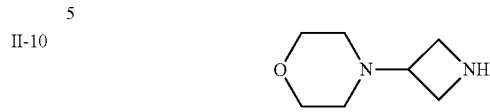

, $R^1 = A^1$

| Intermediate | $R^3$ | $R^4$ | $X^1$ | $X^2$ | MS-ESI [M + H]$^+$ |
|---|---|---|---|---|---|
| II-11 | H | Et | CH | CH | 377.2 |
| II-12 | H | Me | CH | CH | 363.2 |
| II-13 | H | CHF$_2$ | CH | CH | 399.1 |
| II-14 | H | i-Pr | CH | CH | 391.2 |
| II-15 | H | cyclo-Pr | CH | CH | 389.2 |
| II-16 | H | Et | N | CH | 378.2 |
| II-17 | H | Et | CH | N | 378.2 |
| II-18 | H | Et | CH | C—OMe | 407.2 |
| II-19 | H | CHF$_2$ | N | CH | 400.1 |
| II-20 | H | CHF$_2$ | CH | N | 400.1 |
| II-21 | H | CHF$_2$ | CH | C—OMe | 429.1 |
| II-22 | H | CH$_2$—O—CH$_3$ | CH | CH | 393.2 |
| II-23 | Me | CHF$_2$ | CH | CH | 413.2 |

Intermediates R$^2$H (amines)
4-(Azetidin-3-yl)morpholine

Step:1. To the solution of 0.50 g (2.0 mmol) of 1-benzhydrylazetidin-3-one in 20.0 ml of dry DCM 0.21 ml (0.209 g; 2.4 mmol) of morpholine were added, and then the mixture was stirred at room temperature. After 4 h 0.848 g (4.0 mmol) of sodium triacetoxyborohydride were added and stirring was continued at room temperature overnight. Water was added to the reaction mixture and phases were separated. Aqueous phase was extracted 3× with chloroform. Combined organic phases were dried over anhydrous sodium sulphate. The residue obtained after filtration of the drying agent and evaporation of the solvent under reduced pressure was purified on a chromatographic column. Heptane/ethyl acetate/MeOH system from 100/0/0 to 0/95/5 was used for separation. After separation, 0.564 g of 4-[1-(diphenylomethyl)azetidin-3-yl]morpholine were obtained. $^1$H NMR (300 MHz, DMSO) δ 7.45-7.38 (m; 4H); 7.30-7.22 (m; 4H); 7.20-7.13 (m; 2H); 4.41 (s; 1H); 3.58-3.49 (m; 4H); 3.27-3.18 (m; 2H); 2.93-2.82 (m; 1H); 2.80-2.71 (m; 2H); 2.25-2.13 (m; 4H). MS-ESI: (m/z) calculated for $C_{20}H_{24}N_2O$ [M+H]$^+$: 309.20; determined 309.2.

Step 2. To the solution of 114 mg (0.37 mmol) of the product of Step 1 in 4 ml of EtOH 114 mg 10% Pd/C and 10 µl of formic acid were added. The reaction was carried out at room temperature under hydrogen pressure for 48 h. Catalyst was filtered on Celite®, the solid was washed with EtOH, and the filtrate was concentrated on evaporator. 50 mg (95%) of 4-(azetidin-3-yl)morpholine were obtained. $^1$H NMR (300 MHz, CDCl$_3$) δ 3.76-3.67 (m; 4H); 3.55-3.43 (m; 2H); 3.04-2.90 (m; 2H); 2.90-2.80 (m; 1H); 2.39-2.23 (m; 4H). MS-ESI: (m/z) calculated for $C_7H_{14}N_2O$ [M+H]$^+$: 143.12; determined 143.1.

Intermediates R$^2$H presented in Table 1 were obtained analogously as described for the preparation of 4-(azetidin-3-yl)morpholine, replacing morpholine with 2,6-dimethylmorpholine, 1,1-dioxothiomorpholine, 4,4-difluoropiperidine or 3-methoxyazetidine, respectively.

TABLE 10

| R$^2$H | Nazwa | MS-ESI [M + H]$^+$ |
|---|---|---|
| (structure with H$_3$C groups on morpholine-azetidine) | (2R, 6S)-4-(azetidin-3-yl)-2,6-dimethylmorpholine | 171.1 |
| (dioxothiomorpholine-azetidine structure) | 4-(azetidin-3-yl)-1,1-dioxothiomorpholine | 191.1 |
| (difluoropiperidine-azetidine structure) | 1-(azetidin-3-yl)-4,4-difluoropiperidine | 177.1 |

TABLE 10-continued

| R²H | Nazwa | MS-ESI [M + H]⁺ |
|---|---|---|
| 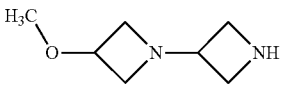 | 3-methoxy-1,3'-biazetidine | 143.1 |

1-(Oxetan-3-yl)piperazine

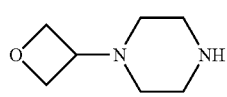

Step 1.

To the solution of 0.23 ml (0.279 g 3.9 mmol) of 3-oxetanone in 39.0 ml of dry DCM 0.60 g (3.2 mmol) of 1-Boc-piperazine were added, and then the mixture was stirred at room temperature. After 4 h, 1.35 g (6.4 mmol) of sodium triacetoxyborohydride were added and stirring was continued at room temperature overnight. Water was added to the reaction mixture and phases were separated. Aqueous phase was extracted 3× with chloroform. Combined organic phases were dried over anhydrous sodium sulphate. After filtration of the drying agent, the solvent was evaporated under reduced pressure. 0.61 g of raw tert-butyl 4-(oxetan-3-yl)piperazin-1-carboxylate were obtained. ¹H NMR (300 MHz, CDCl₃) δ 4.68-4.52 (m; 4H); 3.50-132 (m; 5H); 2.31-2.09 (m; 4H); 1.43 (s; 9H). MS-ESI: (m/z) calculated for $C_{12}H_{22}N_2O_3$ [M+H]⁺: 243.17; determined 243.2.

Step 2.

To the solution of 0.55 g (2.8 mmol) of the product of Step 1 in 28 ml of DCM, 16.8 ml of trifluoroacetic acid were added. The reaction was carried out at room temperature for 2 h. Water was added and the reaction mixture was alkalized with saturated sodium carbonate solution. Phases were separated and aqueous phase was extracted 3× with chloroform. Combined organic phases were dried over anhydrous sodium sulphate. The drying agent was filtered-off and the solvent evaporated under reduced pressure. 0.23 g of raw 1-(oxetan-3-yl)piperazine thus obtained was used for further reaction without purification. ¹H NMR (300 MHz, CDCl₃) δ 4.66-4.56 (m; 4H); 3.66-3.56 (m; 1H); 3.30-3.12 (m; 4H); 2.68-2.51 (m; 4H). MS-ESI: (m/z) calculated for $C_7H_{14}N_2O$ [M+H]⁺: 143.12; determined 143.1.

(1S, 4S)-2-(Oxetan-3-yl)-2,5-diazabicyclo[2.2.1]heptane

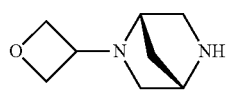 [SMILES: C1OCC1N1C[C@@H]2C[C@H]1CN2]

Prepared analogously as described for the preparation of 1-(oxetan-3-yl)piperazine, starting from z 3-oxetanone and Boc-(1S, 4S)-2,5-diazabicyclo[2.2.1]heptane.

3-Ethyl-1-(piperidin-4-yl)urea

Prepared as described in US2005/197333, Example 41.

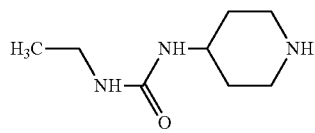

1-Phenyl-3-(piperidin-4-yl)urea

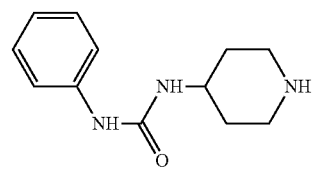 [SMILES: O=C(Nc1ccccc1)NC1CCNCC1]

Prepared analogously as described for the preparation of 3-ethyl-1-(piperidin-4-yl)urea in US2005/197333, Example 41.

Compounds of the Invention

Example 1. 2-((4-(cyclopropanecarbonyl)piperazin-1-yl)methyl)-5-(1H-indol-4-yl)-7-(morpholin-4-yl)pyrazolo[1,5-a]pyrimidine

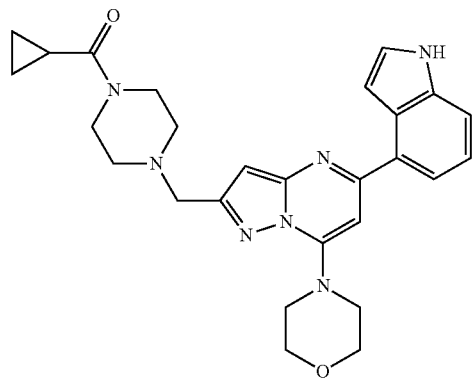 [SMILES: O=C(C1CC1)N1CCN(Cc2cc3nc(-c4cccc5[nH]ccc45)cc(N4CCOCC4)n3n2)CC1]

To the solution of 124 mg (0.357 mmol) of Intermediate II-1 in 4.0 ml of dry DCM, 69.5 mg (0.428 mmol) 1-(cyclopropylcarbonyl)piperazine were added and then stirred at room temperature. After 1 h, 151 mg (0.714 mmol) of sodium triacetoxyborohydride were added and stirring was continued at room temperature for further 1 h. Water was added to the reaction mixture and phases were separated. Aqueous phase was extracted 3× with chloroform. Combined organic phases were dried over anhydrous sodium sulphate. After filtration of the drying agent and evaporation of the solvent under reduced pressure, the residue was purified on a chromatographic plate. CHCl₃/MeOH 90/10 system was used for separation. After separation, 170 mg (98%) of the compound 1 were obtained.

¹H NMR (300 MHz, CDCl₃) δ 8.55 (bs; 1H); 7.61 (dd; J=7.4; 0.8 Hz; 1H); 7.52-7.47 (m; 1H); 7.36-7.27 (m; 2H);

7.13-7.08 (m; 1H); 6.66 (s; 1H); 6.64 (s; 1H); 4.03-3.95 (m; 4H); 3.84 (s; 2H); 3.81-3.65 (m; 8H); 2.71-2.53 (m; 4H); 1.81-1.70 (m; 1H); 1.02-0.95 (m; 2H); 0.79-0.71 (m; 2H). MS-ESI: (m/z) calculated for $C_{27}H_{31}N_7O_2$ $[M+H]^+$: 486.59; determined 486.2.

Compounds of the invention of the Examples 2 to 69 wherein in formula (I) Y represents —$CH_2$— and $R^3$ represents H or alkyl, presented in Table 11, were prepared analogously as in Example 1 starting from suitable Intermediate II-1 to II-9 and II-11 to II-23 and suitable amine $R^2H$.

TABLE 11

Compounds of the invention of formula (I) wherein Y represents —CH$_2$—

| Ex. No. | Chemical name | R$^1$ | R$^2$ | R$^3$ | MS-ESI [M + H]$^+$ | $^1$H NMR (300 MHz) |
|---|---|---|---|---|---|---|
| 2 | 5-(1H-indol-4-yl)-2-((4-(methyl-sulphonyl)piperazin-1-yl)methyl)-7-(morpholin-4-yl)pyrazolo[1,5-a]pyrimidine | indol-4-yl | 4-(methylsulfonyl)piperazin-1-yl | H | 496.2 | (CDCl$_3$) δ: 8.55 (bs; 1H); 7.49-7.38 (m; 2H); 7.32-7.6 (m; 1H); 7.19-7.10 (m; 1H); 6.84-6.80 (m; 1H); 6.7 (s; 1H); 6.49 (s; 1H); 3.89-3.83 (m; 4H); 3.78-3.66 (m; 6H); 3.59-3.51 (m; 4H); 2.75 (s; 3H); 2.64-2.56 (m; 4H) |
| 3 | 5-(1H-indol-4-yl)-2-((4-(4-methylpiperazin-1-yl)piperidin-1-yl)methyl)-7-(morpholin-4-yl)pyrazolo[1,5-a]pyrimidine | indol-4-yl | 4-(4-methylpiperazin-1-yl)piperidin-1-yl | H | 515.3 | (CDCl$_3$) δ 9.56 (s; 1H); 7.62-7.55 (m; 1H); 7.47-7.1 (m; 1H); 7.31-7.21 (m; 2H); 7.11-7.02 (m; 1H); 6.64 (s; 1H); 6.62 (s; 1H); 4.00-3.90 (m; 4H); 3.86-3.62 (m; 6H); 3.19-3.05 (m; 2H); 2.81-2.45 (m; 8H); 2.34 (s; 3H); 2.39-2.29 (m; 1H); 2.21-2.08 (m; 2H); 1.91-1.79 (m; 2H); 1.75-1.54 (m; 2H) |
| 4 | 2-((4-(2-hydroxypropan-2-yl)piperidin-1-yl)methyl)-5-(1H-indol-4-yl)-7-(morpholin-4-yl)pyrazolo[1,5-a]pyrimidine | indol-4-yl | 4-(2-hydroxypropan-2-yl)piperidin-1-yl | H | 475.3 | (CDCl$_3$) δ: 8.57 (bs; 1H); 7.64-7.58 (m; 1H); 7.52-7.46 (m; 1H); 7.36-7.25 (m; 2H); 7.14-7.09 (m; 1H); 6.64 (s; 1H); 6.64 (s; 1H); 4.03-3.95 (m; 4H); 3.82 (s; 2H); 3.81-3.71 (m; 4H); 3.20-3.10 (m; 2H); 2.18-2.03 (m; 2H); 1.81-1.69 (m; 2H); 1.56-1.38 (m; 2H); 1.35-1.30 (m; 1H); 1.18 (s; 6H) |
| 5 | 2-((4-(dimethylamino)piperidin-1-yl)methyl)-5-(1H-indol-4-yl)-7-(morpholin-4-yl)pyrazolo[1,5-a]pyrimidine | indol-4-yl | 4-(dimethylamino)piperidin-1-yl | H | 460.3 | (CDCl$_3$) δ: 8.85 (bs; 1H); 7.60 (d; J = 7.2 Hz; 1H); 7.51 (d; J = 8.2 Hz; 1H); 7.36-7.28 (m; 2H); 7.12-7.08 (m; 1H); 6.65 (s; 1H); 6.61 (s; 1H); 4.04-3.94 (m; 4H); 3.80 (s; 2H); 3.79-3.72 (m; 4H); 3.19-3.07 (m; 2H); 2.60-2.49 (m; 1H); 2.44 (s; 6H); 2.22-2.09 (m; 2H); 1.98-1.86 (m; 2H); 1.76-1.59 (m; 2H) |

TABLE 11-continued

Compounds of the invention of formula (I) wherein Y represents —CH$_2$—

| Ex. No. | Chemical name | R$^1$ | R$^2$ | R$^3$ | MS-ESI [M + H]$^+$ | $^1$H NMR (300 MHz) |
|---|---|---|---|---|---|---|
| 6 | 5-(1H-indol-4-yl)-2-((4-(4-methoxyphenyl)piperazin-1-yl)-methyl)-7-(morpholin-4-yl)-pyrazolo[1,5-a]pyrimidine | 4-indolyl | 4-(4-methoxyphenyl)piperazin-1-yl | H | 524.3 | (CDCl$_3$) δ: 8.52 (bs; 1H); 7.61 (d; J = 7.4 Hz; 1H); 7.49 (d; J = 8.1 Hz; 1H); 7.35-7.27 (m; 2H); 7.14-7.09 (m; 1H); 6.96-6.80 (m; 4H); 6.67 (s; 1H); 6.65 (s; 1H); 4.04-3.95 (m; 4H); 3.88 (s; 2H); 3.82-3.76 (m; 4H); 3.77 (s; 3H); 3.19-3.11 (m; 4H); 2.84-2.74 (m; 4H) |
| 7 | 2-((4-(2-hydroxypropan-2-yl)-piperidin-1-yl)methyl)-5-(5-fluoro-1H-indol-4-yl)-7-(morpholin-4-yl)-pyrazolo[1,5-a]pyrimidine | 5-fluoro-4-indolyl | 4-(2-hydroxypropan-2-yl)piperidin-1-yl | H | 493.3 | (CDCl$_3$) δ 7.39 (dd; J = 8.8; 4.0 Hz; 24H); 7.32 (d; J = 3.2 Hz; 22H); 7.04 (dd; J = 11.1; 8.8 Hz; 1H); 6.95 (d; J = 2.4 Hz; 1H); 6.65 (s; 1H); 6.57 (d; J = 2.3 Hz; 1H); 4.03-3.94 (m; 4H); 3.84-3.73 (m; 6H); 3.19-3.09 (m; J = 11.5 Hz; 2H); 2.16-2.05 (m; 2H); 1.80-1.70 (m; 2H); 1.54-1.46 (m; 1H); 1.46-1.39 (m; 2H); 1.18 (s; 6H) |
| 8 | 2-((4-tert-butylpiperazin-1-yl)-methyl)-5-(1H-indol-4-yl)-7-(morpholin-4-yl)pyrazolo[1,5-a]-pyrimidine | 4-indolyl | 4-tert-butylpiperazin-1-yl | H | 474.3 | (CDCl$_3$) δ 8.66 (bs; 1H); 7.60 (dd; J = 7.4; 0.9 Hz; 1H); 7.52-7.44 (m; 1H); 7.35-7.27 (m; 2H); 7.13-7.05 (m; 1H); 6.63 (s; 1H); 6.63 (s; 1H); 4.02-3.94 (m; 4H); 3.82 (s; 2H); 3.79-3.71 (m; 4H); 2.67 (s; 8H); 1.08 (s; 9H) |
| 9 | 2-(4-((5-(1H-indol-4-yl)-7-(morpholin-4-yl)pyrazolo[1,5-a]-pyrimidin-2-yl)methyl)piperazin-1-yl)-2-methyl-propionamide | 4-indolyl | 4-(1-carbamoyl-1-methylethyl)piperazin-1-yl | H | 503.3 | (CDCl$_3$) δ 8.58 (s; 1H); 7.51 (d; J = 8, Hz; 1H); 7.63-7.58 (m; 1H); 7.13-7.10 (m; 1H); 7.36-7.27 (m; 2H); 6.65 (s; 1H); 6.63 (s; 1H); 4.04-3.96 (m; 4H); 3.83 (s; 2H); 3.81-3.73 (m; 4H); 2.74-2.51 (m; 8H); 1.23 (s; 6H) |

TABLE 11-continued

Compounds of the invention of formula (I) wherein Y represents —CH$_2$—

| Ex. No. | Chemical name | R$^1$ | R$^2$ | R$^3$ | MS-ESI [M + H]$^+$ | $^1$H NMR (300 MHz) |
|---|---|---|---|---|---|---|
| 10 | 2-(4-((5-(5-fluoro-1H-indol-4-yl)-7-(morpholin-4-yl)pyrazolo[1,5-a]-pyrimidin-2-yl)methyl)piperazin-1-yl)-2-methyl-propionamide | 5-fluoro-1H-indol-4-yl | 2-(piperazin-1-yl)-2-methylpropanamide | H | 521.3 | (CDCl$_3$) δ 8.75 (bs; 1H); 7.42-7.35 (m; 1H); 7.33-7.29 (m; 1H); 7.04 (dd; J = 11.2; 8.8 Hz; 1H); 6.7-6.92 (m; 1H); 6.64 (s; 1H); 6.58 (d; J = 2.3 Hz; 1H); 4.03-3.92 (m; 4H); 3.83 (s; 2H); 3.80-3.70 (m; 4H); 2.60 (s; 8H); 1.23 (s; 6H) |
| 11 | 2-((4-tert-butylpiperazin-1-yl)methyl)-5-(5-fluoro-1H-indol-4-yl)-7-(morpholin-4-yl)pyrazolo[1,5-a]-pyrimidine | 5-fluoro-1H-indol-4-yl | 4-tert-butylpiperazin-1-yl | H | 492.3 | (CDCl$_3$) δ 7.39 (dd; J = 8.8; 4.0 Hz; 1H); 7.32 (d; J = 3.2 Hz; 1H); 7.04 (dd; J = 11.1; 8.8 Hz; 1H); 6.92 (dd; J = 3.2; 0.8 Hz; 1H); 6.65 (s; 1H); 6.56 (d; J = 2.3 Hz; 1H); 4.03-3.94 (m; 4H); 3.82 (s; 2H); 3.80-3.74 (m; 4H); 2.67 (s; 8H); 1.08 (s; 9H) |
| 12 | 2-((4-tert-butylpiperazin-1-yl)methyl)-5-(1H-indazol-4-yl)-7-(morpholin-4-yl)pyrazolo[1,5-a]pyrimidine | 1H-indazol-4-yl | 4-tert-butylpiperazin-1-yl | H | 475.3 | (CDCl$_3$ + CD$_3$OD) δ 8.63 (s; 1H); 7.69-7.60 (m; 2H); 7.54-7.46 (m; 1H); 6.69 (s; 1H); 6.64 (s; 1H); 4.06-3.97 (m; 4H); 3.86-3.78 (m; 6H); 2.70 (bs; 8H); 1.11 (s; 9H) |
| 13 | 2-((4-(dimethylamino)piperidin-1-yl)methyl)-5-(5-fluoro-1H-indol-4-yl)-7-(morpholin-4-yl)pyrazolo[1,5-a]pyrimidine | 5-fluoro-1H-indol-4-yl | 4-(dimethylamino)piperidin-1-yl | H | 478.3 | (CDCl$_3$ + CD$_3$OD) δ 7.3 (dd; J = 8.8; 4.0 Hz; 1H); 7..3 (d; J = 3.1 Hz; 1H); 7.02 (dd; J = 11.1; 8.8 Hz; 1H); 6.80 (dd; J = 3.1; 0.8 Hz; 1H); 6.64 (s; 1H); 6.57 (d; J = 2.1 Hz; 1H); 4.05-3.96 (m; 4H); 3.83-3.74 (m; 6H); 3.16-3.05 (m; 2H); 2.28 (s; 6H); 2.24-2.11 (m; 3H); 1.89-1.77 (m; 2H); 1.68-1.53 (m; 2H) |

TABLE 11-continued

Compounds of the invention of formula (I) wherein Y represents —CH$_2$—

| Ex. No. | Chemical name | R$^1$ | R$^2$ | R$^3$ | MS-ESI [M + H]$^+$ | $^1$H NMR (300 MHz) |
|---|---|---|---|---|---|---|
| 14 | 5-(5-fluoro-1H-indol-4-yl)-2-((4-(4-methylpiperazin-1-yl)piperidin-1-yl)methyl)-7-(morpholin-4-yl)-pyrazolo[1,5-a]pyrimidine | 5-fluoro-1H-indol-4-yl | 4-(4-methylpiperazin-1-yl)piperidin-1-yl | H | 533.3 | (CDCl$_3$) δ 7.38-7.2 (m; 1H); 7.30-7.25 (m; 1H); 7.4-6.4 (m; 1H); 6.88-6.82 (m; 3, 1H); 6.64 (s; 1H); 6.5 6 (d; J = 2.0 Hz; 1H); 4.02-3.92 (m; 4H); 3.84-3.70 (m; 6H); 3.16-3.04 (m; 2H); 2.73-2.38 (m; 8H); 2.29 (s; 3H); 2.21-2.08 (m; 3H); 1.92-1.79 (m; 2H); 1.71-1.52 (m; 2H) |
| 15 | 2-((4-(2-hydroxypropan-2-yl)-piperidin-1-yl)methyl)-5-(1H-indazol-4-yl)-7-(morpholin-4-yl)-pyrazolo[1,5-a]pyrimidine | 1H-indazol-4-yl | 4-(2-hydroxypropan-2-yl)piperidin-1-yl | H | 476.3 | (DMSO) δ 13.28 (bs; 1H); 8.76 (d; J = 0.9 Hz; 1H); 7.87 (d; J = 6.8 Hz; 1H); 7.70 (d; J = 8.3 Hz; 1H); 7.55-7.44 (m; 1H); 6.88 (s; 1H); 6.58 (s; 1H); 4.06 (bs; 1H); 3.92-3.80 (m; 8H); 3.64 (s; 2H); 3.03-2.93 (m; 2H); 2.01-1.88 (m; 2H); 1.71-1.60 (m; 2H); 1.37-1.13 (m; Hz; 3H); 1.03 (s; 6H) |
| 16 | 5-(2-aminopyridin-5-yl)-2-((4-tert-butylpiperazin-1-yl)methyl)-7-(morpholin-4-yl)pyrazolo[1,5-a]-pyrimidine | 2-aminopyridin-5-yl | 4-tert-butylpiperazin-1-yl | H | 451.3 | (CDCl$_3$ + CD$_3$OD) δ 8.59 (d; J = 2.2 Hz; 1H); 8.13 (dd; J = 8.8; 2.4 Hz; 1H); 6.67 (d; J = 8.8 Hz; 1H); 6.56 (s; 1H); 6.45 (s; 1H); 4.05-3.95 (m; 4H); 3.85-3.74 (m; 6H); 2.69 (bs; 8H); 1.11 (s; 9H) |
| 17 | 5-(2-aminopyrimidin-5-yl)-2-((4-tert-butylpiperazin-1-yl)methyl)-7-(morpholin-4-yl)pyrazolo[1,5-a]-pyrimidine | 2-aminopyrimidin-5-yl | 4-tert-butylpiperazin-1-yl | H | 452.3 | (DMSO) δ 9.01 (s; 2H); 7.18 (bs; 2H); 6.76 (s; 1H); 6.37 (s; 1H); 3.83 (s; 8H); 3.61 (s; 2H); 2.84 (bs; 8H); 1.12 (s; 9H) |
| 18 | 5-(2-aminopyrimidin-5-yl)-2-((4-(2-hydroxypropan-2-yl)piperidin-1-yl)methyl)-7-(morpholin-4-yl)-pyrazolo[1,5-a]pyrimidine | 2-aminopyrimidin-5-yl | 4-(2-hydroxypropan-2-yl)piperidin-1-yl | H | 453.3 | (DMSO) δ 9.03 (s; 2H); 7.13 (bs; 2H); 6.74 (s; 1H); 6.38 (s; 1H); 4.02 (s; 1H); 3.82 (s; 8H); 3.59 (s; 2H); 2.94 (d; J = 10.8 Hz; 2H); 1.97-1.79 (m; 2H); 1.63 (d; J = 11.5 Hz; 2H); 1.34-1.07 (m; 3H); 1.02 (s; 6H) |

TABLE 11-continued

Compounds of the invention of formula (I) wherein Y represents —CH$_2$—

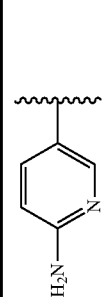

| Ex. No. | Chemical name | R$^1$ | R$^2$ | R$^3$ | MS-ESI [M + H]$^+$ | $^1$H NMR (300 MHz) |
|---|---|---|---|---|---|---|
| 19 | 5-(2-aminopyridin-5-yl)-2-((4-(2-hydroxypropan-2-yl)piperidin-1-yl)methyl)-7-(morpholin-4-yl)-pyrazolo[1,5-a]pyrimidine |  | 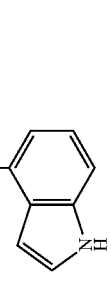 | H | 452.3 | (DMSO) δ 8.79 (d; J = 2.3 Hz; 1H); 8.18 (dd; J = 8.8; 2.5 Hz; 1H); 6.71 (s; 1H); 6.54 (d; J = 8.7 Hz; 1H); 6.47 (s; 1H); 4.07 (s; 1H); 3.90-3.80 (m; 4H); 3.80-3.70 (m; 4H); 3.61 (s; 2H); 3.07-2.87 (m; 2H); 2.05-1.83 (m; 2H); 1.71-1.57 (m; 2H); 1.39-1.10 (m; 3H); 1.03 (s; 6H) |
| 20 | 2-((4-cyclopropyl-piperazin-1-yl)methyl)-5-(1H-indol-4-yl)-7-(morpholin-4-yl)pyrazolo[1,5-a]-pyrimidine |  | 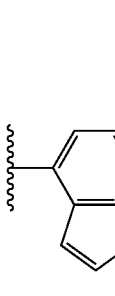 | H | 458.3 | (CDCl$_3$) δ 8.52 (bs; 1H); 7.64-7.56 (m; 1H); 7.53-7.44 (m; 1H); 7.35-7.27 (m; 2H); 7.14-7.07 (m; 1H); 6.64 (s; 1H); 6.63 (s; 1H); 4.04-3.93 (m; 4H); 3.81 (s; 2H); 3.79-3.72 (m; 4H); 2.90-2.46 (m; 8H); 1.68-1.58 (m; 1H); 0.50-0.33 (m; 4H) |
| 21 | 5-(1H-indol-4-yl)-2-((4-methyl-piperazin-1-yl)methyl)-7-(morpholin-4-yl)pyrazolo[1,5-a]-pyrimidine |  | | H | 432.3 | (CDCl$_3$) δ 7.50-7.40 (m; 2H); 7.29-7.26 (m; 1H); 7.21 (dd; J = 8.0; 7.5 Hz; 1H); 6.88 (dd; J = 3.2; 0.9 Hz; 1H); 6.60 (s; 1H); 6.55 (s; 1H); 3.98-3.88 (m; 4H); 3.74 (s; 2H); 3.73-3.66 (m; 4H); 2.56 (bs; 8H); 2.29 (s; 3H) |
| 22 | 2-((4-ethylpiperazin-1-yl)methyl)-5-(1H-indol-4-yl)-7-(morpholin-4-yl)pyrazolo[1,5-a]pyrimidine | 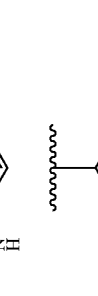 |  | H | 446.3 | (CDCl$_3$) δ 8.55 (bs; 1H); 7.60 (dd; J = 7.4; 0.9 Hz; 1H); 7.34-7.46 (m; 1H); 7.36-7.27 (m; 2H); 7.11-7.05 (m; 1H); 6.64 (s; 1H); 6.62 (s; 1H); 4.06-3.94 (m; 4H); 3.85 (s; 2H); 3.81-3.72 (m; 4H); 2.84 (bs; 8H); 2.72 (q; J = 7.4 Hz; 2H); 1.23 (t; J = 7.2 Hz; 3H) |

TABLE 11-continued

Compounds of the invention of formula (I) wherein Y represents —CH$_2$—

| Ex. No. | Chemical name | R$^1$ | R$^2$ | R$^3$ | MS-ESI [M + H]$^+$ | $^1$H NMR (300 MHz) |
|---|---|---|---|---|---|---|
| 23 | 2-((1,1-dioxothio-morpholin-1-yl)-methyl)-5-(1H-indol-4-yl)-7-(morpholin-4-yl)pyrazolo[1,5-a]-pyrimidine | 1H-indol-4-yl | 1,1-dioxothiomorpholin-1-yl | H | 467.2 | (CDCl$_3$) δ 8.47 (bs; 1H); 7.61 (dd; J = 7.4; 0.9 Hz; 1H); 7.54-7.47 (m; 1H); 7.36-7.28 (m; 2H); 7.14-7.07 (m; 1H); 6.67 (s; 1H); 6.60 (s; 1H); 4.05-3.97 (m; 4H); 3.95 (s; 2H); 3.84-3.73 (m; 4H); 3.20-3.07 (m; 8H) |
| 24 | Methyl 1-((5-(1H-indol-4-yl)-(morpholin-4-yl)pyrazolo[1,5-a]-pyrimidin-2-yl)methyl)piperidin-4-carboxylate | 1H-indol-4-yl | methyl piperidine-4-carboxylate | H | 475.2 | (CDCl$_3$) δ 8.52 (bs; 1H); 7.65-7.58 (m; 1H); 7.54-7.46 (m; 1H); 7.36-7.28 (m; 2H); 7.16-7.08 (m; 1H); 6.64 (s; 1H); 6.63 (s; 1H); 4.05-3.95 (m; 4H); 3.84-3.74 (m; 6H); 3.69 (s; 3H); 3.08-2.97 (m; 2H); 2.38-2.26 (m; 1H); 2.25-2.13 (m; 2H); 1.98-1.81 (m; 4H) |
| 25 | 5-(1H-indol-4-yl)-2-((3-(morpholin-4-yl)methyl)azetidin-1-yl)methyl)-7-(morpholin-4-yl)pyrazolo[1,5-a]-pyrimidine | 1H-indol-4-yl | 3-morpholinoazetidin-1-yl | H | 474.3 | (CDCl$_3$ + CD$_3$OD) δ 7.63-7.49 (m; 2H); 7.41-7.25 (m; 2H); 6.97 (d; J = 3.0 Hz; 1H); 6.67 (s; 1H); 6.58 (s; 1H); 4.08-3.95 (m; 4H); 3.92 (s; 2H); 3.85-3.69 (m; 8H); 3.69-3.57 (m; 4H); 2.36 (bs; 4H) |
| 26 | 2-((4-(cyclopropylmethyl)piperazin-1-yl)methyl)-5-(1H-indol-4-yl)-7-(morpholin-4-yl)pyrazolo[1,5-a]-pyrimidine | 1H-indol-4-yl | 4-(cyclopropylmethyl)piperazin-1-yl | H | 472.3 | (CDCl$_3$ + CD$_3$OD) δ 7.60-7.45 (m; 2H); 7.34-7.23 (m; 2H); 6.95 (dd; J = 3.2; 0.8 Hz; 1H); 6.67 (s; 1H); 6.64 (s; 1H); 4.03-3.94 (m; 4H); 3.83 (s; 2H); 3.80-3.71 (m; 4H); 2.98-2.49 (m; 8H); 2.38 (d; J = 6.7 Hz; 2H); 0.98-0.81 (m; 1H); 0.61-0.46 (m; 2H); 0.20-0.05 (m; 2H) |

TABLE 11-continued

Compounds of the invention of formula (I) wherein Y represents —CH₂—

| Ex. No. | Chemical name | R¹ | R² | R³ | MS-ESI [M + H]⁺ | ¹H NMR (300 MHz) |
|---|---|---|---|---|---|---|
| 27 | 2-((4-cyclopentylpiperazin-1-yl)methyl)-5-(1H-indol-4-yl)-7-(morpholin-4-yl)pyrazolo[1,5-a]pyrimidine | 4-indolyl | 4-cyclopentylpiperazin-1-yl | H | 486.3 | (CDCl₃ + CD₃OD) δ 7.59-7.45 (m; 2H); 7.34-7.23 (m; 2H); 6.99-6.92 (m; 1H); 6.67 (s; 1H); 6.63 (s; 1H); 4.04-3.94 (m; 4H); 3.85-3.72 (m; 6H); 2.86-2.50 (m; 9H); 1.95-1.82 (m; 2H); 1.80-1.63 (m; 2H); 1.63-1.40 (m; 4H) |
| 28 | 2-((4-tert-butylpiperidin-1-yl)methyl)-5-(1H-indol-4-yl)-7-(morpholin-4-yl)pyrazolo[1,5-a]pyrimidine | 4-indolyl | 4-tert-butylpiperidin-1-yl | H | 473.3 | (CDCl₃) δ 8.53 (bs; 1H); 7.61 (dd; J = 7.4; 0.8 Hz; 1H); 7.48 (d; J = 8.1 Hz; 1H); 7.35-7.27 (m; 2H); 7.15-7.08 (m; 1H); 6.63 (s; 1H); 6.63 (s; 1H); 4.06-3.92 (m; 4H); 3.83-3.70 (m; 6H); 3.18-3.08 (m; 2H); 2.12-2.01 (m; 2H); 1.71-1.60 (m; 2H); 1.48-1.29 (m; 2H); 1.07-0.91 (m; 1H); 0.85 (s; 9H) |
| 29 | 5-(1H-6-azaindol-4-yl)-2-(4-(2-hydroxypropan-2-yl)piperidin-1-yl)methyl)-7-(morpholin-4-yl)pyrazolo[1,5-a]pyrimidine | 4-(6-azaindolyl) | 4-(2-hydroxypropan-2-yl)piperidin-1-yl | H | 476.3 | (CDCl₃) δ 10.43 (bs; 1H); 8.80-8.78 (m; 1H); 8.72 (s; 1H); 7.51 (d; J = 3.1 Hz; 1H); 7.18 (d; J = 2.6 Hz; 1H); 6.65 (s; 1H); 6.61 (s; 1H); 4.02-3.90 (m; 4H); 3.84-3.72 (m; 6H); 3.20-3.09 (m; 2H); 2.16-2.03 (m; 2H); 1.80-1.70 (m; 2H); 1.53-1.31 (m; 3H); 1.18 (s; 6H) |
| 30 | 5-(1H-6-azaindol-4-yl)-2-((4-tert-butylpiperazin-1-yl)methyl)-7-(morpholin-4-yl)pyrazolo[1,5-a]pyrimidine | 4-(6-azaindolyl) | 4-tert-butylpiperazin-1-yl | H | 475.3 | (DMSO) δ 9.76 (s; 1H); 8.84 (s; 1H); 8.73 (s; 1H); 7.52 (d; J = 3.0 Hz; 1H); 7.21 (d; J = 3.0 Hz; 1H); 6.64 (s; 1H); 6.60 (s; 1H); 4.06-3.91 (m; 4H); 3.88-3.74 (m; 6H); 2.69 (bs; 8H); 1.09 (s; 9H) |

TABLE 11-continued

Compounds of the invention of formula (I) wherein Y represents —CH$_2$—

| Ex. No. | Chemical name | R$^1$ | R$^2$ | R$^3$ | MS-ESI [M + H]$^+$ | $^1$H NMR (300 MHz) |
|---|---|---|---|---|---|---|
| 31 | 5-(1H-indol-4-yl)-2-((3-(1,1-dioxothiomorpholin-4-yl)azetidin-1-yl)methyl)-7-(morpholin-4-yl)-pyrazolo[1,5-a]pyrimidine | 4-indolyl | 3-(1,1-dioxothiomorpholin-4-yl)azetidin-1-yl | H | 522.2 | (CDCl$_3$ + CD$_3$OD) δ 7.59-7.52 (m; 2H); 7.36 (d; J = 3.2 Hz; 1H); 7.33-7.27 (m; 1H); 6.97 (dd; J = 3.2; 0.9 Hz; 1H); 6.70 (s; 1H); 6.60 (s; 1H); 4.06-3.95 (m; 6H); 3.84-3.69 (m; 6H); 3.26-3.15 (m; 2H); 3.13-3.05 (m; 4H); 2.89-2.80 (m; 4H) |
| 32 | 5-(1H-7-azaindol-4-yl)-2-(4-tert-butylpiperazin-1-yl)methyl)-7-(morpholin-4-yl)pyrazolo[1,5-a]-pyrimidine | 4-(7-azaindolyl) | 4-tert-butylpiperazin-1-yl | H | 475.3 | (CDCl$_3$) δ 10.55 (bs; 1H); 8.47 (d; J = 5.1 Hz; 1H); 7.59 (d; J = 5.1 Hz; 1H); 7.53-7.48 (m; 1H); 7.10-7.02 (m; 1H); 6.69 (s; 1H); 6.67 (s; 1H); 4.07-3.95 (m; 4H); 3.88-3.76 (m; 6H); 2.80-2.55 (m; 8H); 1.08 (s; 9H) |
| 33 | 5-(1H-7-azaindol-4-yl)-2-(4-(2-hydroxypropan-2-yl)piperidin-1-yl)methyl)-7-(morpholin-4-yl)pyrazolo[1,5-a]-pyrimidine | 4-(7-azaindolyl) | 4-(2-hydroxypropan-2-yl)piperidin-1-yl | H | 476.3 | (CDCl$_3$) δ 10.54 (bs; 1H); 8.46 (d; J = 5.0 Hz; 1H); 7.59 (d; J = 5.1 Hz; 1H); 7.53-7.46 (m; 1H); 7.09-7.02 (m; 1H); 6.70 (s; 1H); 6.67 (s; 1H); 4.09-3.94 (m; 4H); 3.90-3.70 (m; 6H); 3.22-3.05 (m; 2H); 2.18-2.02 (m; 2H); 1.84-1.67 (m; 2H); 1.56-1.32 (m; 3H); 1.19 (s; 6H) |
| 34 | 5-(1H-indol-4-yl)-2-((4-(oxetan-3-yl)piperidin-1-yl)methyl)-7-(morpholin-4-yl)pyrazolo[1,5-a]-pyrimidine | 4-indolyl | 4-(oxetan-3-yl)piperazin-1-yl | H | 474.3 | (CDCl$_3$) δ 8.62 (bs; 1H); 7.60 (dd; J = 7.4; 0.8 Hz; 1H); 7.48 (d; J = 8.1 Hz; 1H); 7.34-7.27 (m; 2H); 7.13-7.08 (m; 1H); 6.64 (s; 1H); 6.63 (s; 1H); 4.70-4.59 (m; J = 6.4 Hz; 4H); 4.02-3.95 (m; 4H); 3.84 (s; 2H); 3.80-3.73 (m; 4H); 3.52 (p; J = 6.5 Hz; 1H); 2.81-2.55 (m; 4H); 2.53-2.27 (m; 4H) |

TABLE 11-continued

Compounds of the invention of formula (I) wherein Y represents —CH₂—

| Ex. No. | Chemical name | R¹ | R² | R³ | MS-ESI [M + H]⁺ | ¹H NMR (300 MHz) |
|---|---|---|---|---|---|---|
| 35 | 5-(1H-5-fluoroindol-4-yl)-2-((4-(oxetan-3-yl)piperidin-1-yl)methyl)-7-(morpholin-4-yl)pyrazolo[1,5-a]-pyrimidine | 5-fluoro-1H-indol-4-yl | 4-(oxetan-3-yl)piperidin-1-yl | H | 492.3 | (CDCl₃) δ 8.54 (bs; 1H); 7.37 (dd; J = 8.7; 3.9 Hz; 1H); 7.33-7.28 (m; 1H); 7.08-6.99 (m; 1H); 6.98-6.93 (m; 1H); 6.63 (s; 1H); 6.5 7 (d; J = 2.2 Hz; 1H); 4.72-4.57 (m; 4H); 4.04-3.91 (m; 4H); 3.84 (s; 2H); 3.81-3.70 (m; 4H); 3.52 (p; J = 6.6 Hz; 1H); 2.81-2.55 (m; 4H); 2.52-2.28 (m; 4H) |
| 36 | 5-(1H-indol-4-yl)-2-(((1S, 4S)-2-(oxetan-3-yl)-2,5-diazabicyclo[2.2.1]hept-2-yl)methyl)-7-(morpholin-4-yl)pyrazolo[1,5-a]-pyrimidine | 1H-indol-4-yl | (1S,4S)-2-(oxetan-3-yl)-2,5-diazabicyclo[2.2.1]hept-5-yl | H | 486.3 | (CDCl₃ + CD₃OD) δ 7.59-7.51 (m; 2H); 7.35 (d; J = 3.2 Hz; 1H); 7.33-7.25 (m; 1H); 6.98-6.93 (m; J = 3.2; 0.8 Hz; 1H); 6.69 (s; 1H); 6.65 (s; 1H); 4.81-4.68 (m; 2H); 4.68-4.54 (m; 2H); 4.05-3.98 (m; 6H); 3.97-3.91 (m; 4H); 3.83-3.76 (m; 4H); 3.61-3.56 (m; 1H); 3.35-3.31 (m; 1H); 2.70-2.62 (m; 1H); 1.89-1.80 (m; 1H); 1.79-1.70 (m; 1H) |
| 37 | 3-ethyl-1-(1-((5-((1H-indol-4-yl)pyrazolo[1,5-a]pyrimidin-2-yl)methyl)piperidin-4-yl)urea | 1H-indol-4-yl | 4-(3-phenylureido)piperidin-1-yl | H | 551.3 | (DMSO) δ 11.36 (s; 1H); 8.32 (s; 1H); 7.69-7.62 (m; 1H); 7.58-7.52 (m; 1H); 7.51-7.46 (m; 1H); 7.40-7.32 (m; 2H); 7.27-7.16 (m; 3H); 7.14-7.08 (m; 1H); 6.91-6.83 (m; 1H); 6.78 (s; 1H); 6.5 2 (s; 1H); 6.19-6.09 (m; 1H); 3.94-3.74 (m; 8H); 3.69 (s; 2H); 3.58-3.41 (m; 1H); 2.90-2.73 (m; 2H); 2.34-2.12 (m; 2H); 1.91-1.76 (m; 2H); 1.52-1.34 (m; 2H) |
| 38 | 1-phenyl-3-(1-((5-(1H-indol-4-yl)-7-(morpholin-4-yl)pyrazolo[1,5-a]-pyrimidin-2-yl)methyl)piperidin-4-yl)urea | 1H-indol-4-yl | 4-(3-ethylureido)piperidin-1-yl | H | 503.3 | (DMSO) δ 11.35 (bs; 1H); 7.65 (d; J = 6.6 Hz; 1H); 7.54 (d; J = 8.1 Hz; 1H); 7.51-7.46 (m; 1H); 7.27-7.18 (m; 1H); 7.13-7.07 (m; 1H); 6.77 (s; 1H); 6.50 (s; 1H); 5.74 (d; J = 7.9 Hz; 1H); 5.66 (t; J = 5.5 Hz; 1H); 3.92-3.73 (m; 8H); 3.65 (s; 2H); 2.98 (d; J = 7.7 Hz; 2H); 2.86-2.71 (m; 2H); 2.20-2.05 (m; 2H); 1.81-1.66 (m; 2H); 1.38-1.19 (m; 3H); 0.96 (t; J = 7.7 Hz; 3H) |

TABLE 11-continued

Compounds of the invention of formula (I) wherein Y represents —CH₂—

| Ex. No. | Chemical name | R¹ | R² | R³ | MS-ESI [M + H]⁺ | ¹H NMR (300 MHz) |
|---|---|---|---|---|---|---|
| 39 | 2-((4-tert-butylpiperazin-1-yl)methyl)-5-(5-fluoro-1H-indol-4-yl)-7-(morpholin-4-yl)pyrazolo[1,5-a]pyrimidine | 5-fluoro-1H-indol-4-yl | 4-tert-butylpiperazin-1-ylmethyl | H | 492.3 | (CDCl₃) 7.95 (dd; J = 2.2; 11.1; 1H); 7.49-7.56 (m; 1H); 7.31 (dd; J = 2.6; 3.3; 1H); 7.18 (dd; J = 2.2; 8.8; 1H); 6.71 (s; 1H); 6.57 (s; 1H); 4.03-3.94 (m; 4H); 3.82 (s; 2H); 3.80-3.74 (m; 4H); 2.67 (s; 8H); 1.08 (s; 9H) |
| 40 | 2-((4-tert-butylpiperazin-1-yl)methyl)-5-(1H-indol-4-yl)-7-(morpholin-4-yl)pyrazolo[1,5-a]pyrimidine | 1H-indol-4-yl | 4-tert-butylpiperazin-1-ylmethyl | Me | 488.3 | (CDCl₃) δ 8.86 (bs; 1H); 7.61 (d; J = 7.4 Hz; 1H); 7.44 (d; J = 7.4 Hz; 1H); 7.34-7.24 (m; 3H); 6.58 (s; 1H); 4.00-3.87 (m; 4H); 3.83 (s; 2H); 3.77-3.61 (m; 4H); 2.80-2.59 (m; 8H); 2.43 (s; 3H); 1.10 (s; 9H) |
| 41 | 2-((4-(2-hydroxypropan-2-yl)piperidin-1-yl)methyl)-5-(1H-indol-4-yl)-3-methyl-7-(morpholin-4-yl)-pyrazolo[1,5-a]pyrimidine | 1H-indol-4-yl | (4-(2-hydroxypropan-2-yl)piperidin-1-yl)methyl | Me | 489.3 | (CDCl₃) δ 8.65 (bs; 1H); 7.65-7.60 (m; 1H); 7.51-7.45 (m; 1H); 7.35-7.30 (m; 1H); 7.30-7.26 (m; 2H); 6.62 (s; 1H); 4.04-3.90 (m; 6H); 3.79-3.71 (m; 4H); 3.29-3.19 (m; 2H); 2.44 (s; 3H); 2.32-2.19 (m; 2H); 1.83-1.70 (m; 2H); 1.61-1.44 (m; 2H); 1.36-1.23 (m; 1H); 1.17 (s; 6H) |
| 42 | 5-(2-ethylbenzimidazol-1-yl)-2-(4-(methylsulphonyl)piperazin-1-yl)methyl)-7-(morpholin-4-yl)pyrazolo[1,5-a]pyrimidine | 2-ethylbenzimidazol-1-yl | (4-(methylsulphonyl)piperazin-1-yl)methyl | H | 525.2 | (CDCl₃) δ 7.83-7.77 (m; 1H); 7.48-7.42 (m; 1H); 7.34-7.22 (m; 2H); 6.59 (s; 1H); 6.20 (s; 1H); 4.03-3.96 (m; 4H); 3.91-3.81 (m; 6H); 3.34-3.24 (m; 4H); 3.12 (q; J = 7.5 Hz; 2H); 2.79 (s; 3H); 2.76-2.67 (m; 4H); 1.42 (t; J = 7.5 Hz; 3H) |

TABLE 11-continued

Compounds of the invention of formula (I) wherein Y represents —CH₂—

| Ex. No. | Chemical name | R¹ | R² | R³ | MS-ESI [M + H]⁺ | ¹H NMR (300 MHz) |
|---|---|---|---|---|---|---|
| 43 | 5-(2-ethylbenzimidazol-1-yl)-2-((4-(dimethylamino)piperidin-1-yl)methyl)-7-(morpholin-4-yl)-pyrazolo[1,5-a]pyrimidine | 2-ethylbenzimidazol-1-yl | 4-(dimethylamino)piperidin-1-yl | H | 489.3 | (CDCl₃) δ 7.84-7.72 (m; 1H); 7.49-7.38 (m; 1H); 7.35-7.17 (m; 2H); 6.60 (s; 1H); 6.18 (s; 1H); 4.04-3.94 (m; 4H); 3.91-3.82 (m; 4H); 3.79 (s; 2H); 3.19-3.04 (m; 3H); 2.40 (s; 6H); 2.24-2.09 (m; 2H); 1.96-1.84 (m; 2H); 1.73-1.58 (m; 2H); 1.43 (t; J = 7.5 Hz; 3H); 1.33-1.24 (m; 2H) |
| 44 | 5-(2-ethylbenzimidazol-1-yl)-2-((4-(4-methylpiperazin-1-yl)piperidin-1-yl)methyl)-7-(morpholin-4-yl)-pyrazolo[1,5-a]pyrimidine | 2-ethylbenzimidazol-1-yl | 4-(4-methylpiperazin-1-yl)piperidin-1-yl | H | 544.4 | (CDCl₃) δ 7.82-7.76 (m; 1H); 7.48-7.42 (m; 1H); 7.33-7.22 (m; 2H); 6.60 (s; 1H); 6.19 (s; 1H); 4.02-3.95 (m; 4H); 3.89-3.82 (m; 4H); 3.82-3.78 (m; 2H); 3.17-3.04 (m; 4H); 2.82-2.45 (m; 8H); 2.32 (s; 3H); 2.39-2.29 (m; 1H); 2.21-2.08 (m; 2H); 1.91-1.79 (m; 2H); 1.75-1.54 (m; 2H); 1.42 (t; J = 7.5 Hz; 3H) |
| 45 | 5-(2-ethylbenzimidazol-1-yl)-2-((4-(4-methoxyphenyl)piperazin-1-yl)methyl)-7-(morpholin-4-yl)-pyrazolo[1,5-a]pyrimidine | 2-ethylbenzimidazol-1-yl | 4-(4-methoxyphenyl)piperazin-1-yl | H | 553.3 | (CDCl₃) δ 7.87-7.76 (m; 1H); 7.50-7.39 (m; 1H); 7.36-7.21 (m; 2H); 6.97-6.80 (m; 4H); 6.64 (s; 1H); 6.19 (s; 1H); 4.05-3.96 (m; 4H); 3.94-3.82 (m; 6H); 3.77 (s; 3H); 3.22-3.08 (m; 6H); 2.86-2.75 (m; 4H); 1.43 (t; J = 7.5 Hz; 3H) |
| 46 | 5-(2-ethylbenzimidazol-1-yl)-2-((4-(2-hydroxypropan-2-yl)piperidin-1-yl)methyl)-7-(morpholin-4-yl)-pyrazolo[1,5-a]pyrimidine | 2-ethylbenzimidazol-1-yl | 4-(2-hydroxypropan-2-yl)piperidin-1-yl | H | 504.3 | (CDCl₃) δ 7.85-7.72 (m; 1H); 7.49-7.39 (m; 1H); 7.36-7.18 (m; 2H); 6.62 (s; 1H); 6.18 (s; 1H); 4.06-3.93 (m; 4H); 3.92-3.83 (m; 4H); 3.80 (s; 2H); 3.21-3.07 (m; 4H); 3.01 (d; J = 7.5 Hz; 2H); 2.18-2.05 (m; 2H); 1.83-1.70 (m; 2H); 1.42 (t; J = 7.5 Hz; 3H); 1.37-1.27 (m; 1H); 1.19 (s; 6H) |

TABLE 11-continued

Compounds of the invention of formula (I) wherein Y represents —CH$_2$—

| Ex. No. | Chemical name | R$^1$ | R$^2$ | R$^3$ | MS-ESI [M + H]$^+$ | $^1$H NMR (300 MHz) |
|---|---|---|---|---|---|---|
| 47 | 5-(2-ethylbenzimidazol-1-yl)-2-((4-tert-butylpiperazin-1-yl)methyl)-7-(morpholin-4-yl)pyrazolo[1,5-a]pyrimidine | 2-ethylbenzimidazol-1-yl | (4-tert-butylpiperazin-1-yl)methyl | H | 503.3 | (CDCl$_3$) δ 7.83-7.76 (m; 1H); 7.48-7.41 (m; 1H); 7.35-7.22 (m; 2H); 6.60 (s; 1H); 6.19 (s; 1H); 4.04-3.96 (m; 4H); 3.91-3.81 (m; 6H); 3.13 (q; J = 7.5 Hz; 2H); 2.93-2.66 (m; 8H); 1.43 (t; J = 7.5 Hz; 3H); 1.20 (s; 9H) |
| 48 | 5-(2-methylbenzimidazol-1-yl)-2-((4-tert-butylpiperazin-1-yl)methyl)-7-(morpholin-4-yl)pyrazolo[1,5-a]pyrimidine | 2-methylbenzimidazol-1-yl | (4-tert-butylpiperazin-1-yl)methyl | H | 489.3 | (CDCl$_3$) δ 7.79-7.70 (m; 1H); 7.50-7.43 (m; 1H); 7.35-7.21 (m; 2H); 6.60 (s; 1H); 6.17 (s; 1H); 4.02-3.95 (m; 4H); 3.90-3.83 (m; 4H); 3.82 (s; 2H); 2.76 (s; 3H); 2.71-2.59 (m; 8H); 1.08 (s; 9H) |
| 49 | 5-(2-methylbenzimidazol-1-yl)-2-(((4-(2-hydroxypropan-2-yl)piperidin-1-yl)methyl)-7-(morpholin-4-yl)pyrazolo[1,5-a]pyrimidine | 2-methylbenzimidazol-1-yl | (4-(2-hydroxypropan-2-yl)piperidin-1-yl)methyl | H | 490.3 | (CDCl$_3$) δ 7.79-7.72 (m; 1H); 7.52-7.45 (m; 1H); 7.34-7.20 (m; 2H); 6.61 (s; 1H); 6.18 (s; 1H); 4.04-3.95 (m; 4H); 3.91-3.82 (m; 4H); 3.79 (s; 2H); 3.18-3.09 (m; 2H); 2.77 (s; 3H); 2.16-2.03 (m; 2H); 1.82-1.71 (m; 2H); 1.55-1.37 (m; 2H); 1.37-1.23 (m; 1H); 1.19 (s; 6H) |
| 50 | 5-(2-(difluoromethyl)benzimidazol-1-yl)-2-((4-tert-butylpiperazin-1-yl)methyl)-7-(morpholin-4-yl)pyrazolo[1,5-a]pyrimidine | 2-(difluoromethyl)benzimidazol-1-yl | (4-tert-butylpiperazin-1-yl)methyl | H | 525.3 | (CDCl$_3$) δ 7.96-7.87 (m; 1H); 7.70-7.61 (m; 1H); 7.47-7.37 (m; 2H); 7.31 (t; J = 54.0 Hz; 1H); 6.60 (s; 1H); 6.31 (s; 1H); 4.03-3.95 (m; 4H); 3.94-3.87 (m; 4H); 3.82 (s; 2H); 2.83-2.56 (m; 8H); 1.09 (s; 9H) |
| 51 | 5-(2-(difluoromethyl)benzimidazol-1-yl)-2-((4-(2-hydroxypiperidin-1-yl)methyl)-7-(morpholin-4-yl)pyrazolo[1,5-a]pyrimidine | 2-(difluoromethyl)benzimidazol-1-yl | (4-(2-hydroxypiperidin-1-yl)methyl | H | 526.3 | (CDCl$_3$) δ 7.92 (dd; J = 5.2; 4.1 Hz; 1H); 7.70-7.62 (m; 1H); 7.47-7.38 (m; 2H); 7.31 (t; J = 54.0 Hz; 1H); 6.62 (s; 1H); 6.32 (s; 1H); 4.03-3.95 (m; 4H); 3.94-3.87 (m; 4H); 3.82 (s; 2H); 3.23-3.08 (m; 2H); 2.21-2.08 (m; 2H); 1.83-1.70 (m; 2H); 1.56-1.39 (m; 2H); 1.38-1.2 (m; 1H); 1.19 (s; 6H) |

TABLE 11-continued

Compounds of the invention of formula (I) wherein Y represents —CH$_2$—

| Ex. No. | Chemical name | R$^1$ | R$^2$ | R$^3$ | MS-ESI [M + H]$^+$ | $^1$H NMR (300 MHz) |
|---|---|---|---|---|---|---|
| 52 | 5-(2-iso-propylbenzimidazol-1-yl)-2-((4-tert-butylpiperazin-1-yl)methyl)-7-(morpholin-4-yl)-pyrazolo[1,5-a]pyrimidine | 2-isopropylbenzimidazol-1-yl | 4-tert-butylpiperazin-1-yl | H | 517.3 | (CDCl$_3$) δ 7.84-7.79 (m; 1H); 7.43-7.36 (m; 1H); 7.33-7.20 (m; 2H); 6.60 (s; 1H); 6.16 (s; 1H); 4.02-3.96 (m; 4H); 3.89-3.84 (m; 4H); 3.83 (s; 2H); 3.66-3.55 (m; 1H); 2.69 (bs; 8H); 1.42 (d; J = 6.9 Hz; 6H); 1.10 (s; 9H) |
| 53 | 5-(2-iso-propylbenzimidazol-1-yl)-2-((4-(2-hydroxypropan-2-yl)piperidin-1-yl)methyl)-7-(morpholin-4-yl)pyrazolo[1,5-a]pyrimidine | 2-isopropylbenzimidazol-1-yl | 4-(2-hydroxypropan-2-yl)piperidin-1-yl | H | 518.3 | (CDCl$_3$) δ 7.84-7.77 (m; 1H); 7.42-7.35 (m; 1H); 7.33-7.20 (m; 2H); 6.64 (s; 1H); 6.18 (s; 1H); 4.03-3.93 (m; 4H); 3.91-3.80 (m; 6H); 3.61 (hept; J = 6.8 Hz; 1H); 3.24-3.12 (m; 2H); 2.23-2.09 (m; 2H); 1.83-1.74 (m; 2H); 1.56-1.46 (m; 2H); 1.42 (d; J = 6.8 Hz; 6H); 1.29-1.23 (m; 1H); 1.19 (s; 6H) |
| 54 | 5-(2-cyclopropylbenzimidazol-1-yl)-2-((4-tert-butylpiperazin-1-yl)methyl)-7-(morpholin-4-yl)-pyrazolo[1,5-a]pyrimidine | 2-cyclopropylbenzimidazol-1-yl | 4-tert-butylpiperazin-1-yl | H | 515.3 | (CDCl$_3$) δ 7.73-7.67 (m; 1H); 7.56-7.49 (m; 1H); 7.34-7.19 (m; 2H); 6.62 (s; 1H); 6.29 (s; 1H); 4.03-3.94 (m; 4H); 3.89-3.79 (m; 6H); 2.71 (bs; 8H); 2.41-2.30 (m; 1H); 1.42-1.32 (m; 2H); 1.20-1.03 (m; 11H) |
| 55 | 5-(2-cyclopropylbenzimidazol-1-yl)-2-((4-(2-hydroxypropan-2-yl)piperidin-1-yl)methyl)-7-(morpholin-4-yl)pyrazolo[1,5-a]pyrimidine | 2-cyclopropylbenzimidazol-1-yl | 4-(2-hydroxypropan-2-yl)piperidin-1-yl | H | 516.3 | (CDCl$_3$) δ 7.73-7.67 (m; 1H); 7.56-7.49 (m; 1H); 7.31-7.22 (m; 2H); 6.65 (s; 1H); 6.30 (s; 1H); 4.02-3.97 (m; 4H); 3.89-3.79 (m; 6H); 3.21-3.11 (m; 2H); 2.43-2.31 (m; 1H); 2.19-2.09 (m; 2H); 1.81-1.75 (m; 2H); 1.56-1.44 (m; 2H); 1.40-1.35 (m; 2H); 1.29-1.23 (m; 1H); 1.19 (s; 6H); 1.14-1.07 (m; 2H) |

TABLE 11-continued

Compounds of the invention of formula (I) wherein Y represents —CH$_2$—

| Ex. No. | Chemical name | R$^1$ | R$^2$ | R$^3$ | MS-ESI [M + H]$^+$ | $^1$H NMR (300 MHz) |
|---|---|---|---|---|---|---|
| 56 | 5-(2-ethylimidazo[4,5-b]pyridin-1-yl)-2-((4-tert-butylpiperazin-1-yl)methyl)-7-(morpholin-4-yl)-pyrazolo[1,5-a]pyrimidine | 2-ethylimidazo[4,5-b]pyridin-1-yl | 4-tert-butylpiperazin-1-ylmethyl | H | 504.3 | (CDCl$_3$) δ 8.55 (dd; J = 4.8; 1.5 Hz; 1H); 7.77 (dd; J = 8.1; 1.5 Hz; 1H); 7.20 (dd; J = 8.1; 4.8 Hz; 1H); 6.61 (s; 1H); 6.09 (s; 1H); 4.02-3.98 (m; 4H); 3.91-3.86 (m; 4H); 3.82 (s; 2H); 3.15 (q; J = 7.5 Hz; 2H); 2.66 (bs; 8H); 1.47 (t; J = 7.5 Hz; 3H); 1.08 (s; 9H) |
| 57 | 5-(2-ethylimidazo[4,5-c]pyridin-1-yl)-2-((4-tert-butylpiperazin-1-yl)methyl)-7-(morpholin-4-yl)-pyrazolo[1,5-a]pyrimidin | 2-ethylimidazo[4,5-c]pyridin-1-yl | 4-tert-butylpiperazin-1-ylmethyl | H | 504.3 | (CDCl$_3$) δ 9.10 (d; J = 1.0 Hz; 1H); 8.44 (d; J = 5.6 Hz; 1H); 7.38 (dd; J = 5.6; 1.0 Hz; 1H); 6.61 (s; 1H); 6.10 (s; 1H); 4.02-3.97 (m; 4H); 3.93-3.87 (m; 4H); 3.82 (s; 2H); 3.13 (q; J = 7.5 Hz; 2H); 2.66 (bs; 8H); 1.45 (t; J = 7.5 Hz; 3H); 1.08 (s; 9H) |
| 58 | 5-(2-ethyl-5-methoxybenzimidazol-1-yl)-2-((4-tert-butylpiperazin-1-yl)methyl)-7-(morpholin-4-yl)-pyrazolo[1,5-a]pyrimidin | 2-ethyl-5-methoxybenzimidazol-1-yl | 4-tert-butylpiperazin-1-ylmethyl | H | 533.3 | (CDCl$_3$) δ 7.35-7.31 (m; 1H); 7.29 (d; J = 2.5 Hz; 1H); 6.89 (dd; J = 8.8; 2.5 Hz; 1H); 6.59 (s; 1H); 6.15 (s; 1H); 4.03-3.95 (m; 4H); 3.89-3.82 (m; 7H); 3.81 (s; 2H); 3.10 (q; J = 7.5 Hz; 2H); 2.66 (bs; 8H); 1.42 (t; J = 7.5 Hz; 3H); 1.08 (s; 9H) |
| 59 | 5-(2-ethyl-5-methoxybenzimidazol-1-yl)-2-((4-(2-hydroxypropan-2-yl)piperidin-1-yl)methyl)-7-(morpholin-4-yl)pyrazolo[1,5-a]pyrimidine | 2-ethyl-5-methoxybenzimidazol-1-yl | 4-(2-hydroxypropan-2-yl)piperidin-1-ylmethyl | H | 534.3 | (DMSO) δ 7.50 (d; J = 8.8 Hz; 1H); 7.22 (d; J = 2.5 Hz; 1H); 6.86 (dd; J = 8.8; 2.5 Hz; 1H); 6.51 (s; 1H); 6.49 (s; 1H); 4.05 (s; 1H); 3.92-3.80 (m; 8H); 3.80 (s; 3H); 3.63 (s; 2H); 3.08-2.90 (m; 4H); 2.01-1.86 (m; 2H); 1.71-1.57 (m; 2H); 1.34-1.12 (m; 6H); 1.02 (s; 6H) |
| 60 | 5-(2-difluoromethyl-5-methoxy-benzimidazol-1-yl)-2-((4-tert-butylpiperazin-1-yl)methyl)-7-(morpholin-4-yl)pyrazolo[1,5-a]-pyrimidine | 2-difluoromethyl-5-methoxybenzimidazol-1-yl | 4-tert-butylpiperazin-1-ylmethyl | H | 555.3 | (DMSO) δ 7.58-7.53 (m; 1H); 7.35 (d; J = 2.1 Hz; 1H); 7.27 (t; J = 54 Hz; 1H); 7.07 (dd; J = 11.1; 2.1 Hz; 1H); 6.59 (s; 1H); 6.29 (s; 1H); 4.02-3.96 (m; 4H); 3.93-3.86 (m; 7H); 3.80 (s; 2H); 2.65 (bs; 8H); 1.08 (s; 9H) |

TABLE 11-continued

Compounds of the invention of formula (I) wherein Y represents —CH₂—

| Ex. No. | Chemical name | R¹ | R² | R³ | MS-ESI [M + H]⁺ | ¹H NMR (300 MHz) |
|---|---|---|---|---|---|---|
| 61 | 5-(2-(difluoromethyl)-5-methoxybenzimidazol-1-yl)-2-((4-(2-hydroxypropan-2-yl)piperidin-1-yl)methyl)-7-(morpholin-4-yl)pyrazolo[1,5-a]pyrimidine | 2-(difluoromethyl)-5-methoxybenzimidazol-1-yl | 4-(2-hydroxypropan-2-yl)piperidin-1-yl | H | 556.3 | (CDCl₃) δ 7.56 (d; J = 9.0 Hz; 1H); 7.35 (d; J = 2.4 Hz; 1H); 7.28 (t; J = 60 Hz; 1H); 7.07 (dd; J = 9.0; 2.4 Hz; 1H); 6.60 (s; 1H); 6.30 (s; 1H); 4.03-3.95 (m; 4H); 3.93-3.86 (m; 7H); 3.78 (s; 2H); 3.18-3.03 (m; 2H); 2.17-2.01 (m; 2H); 1.90-1.68 (m; 3H); 1.55-1.36 (m; 2H); 1.36-1.22 (m; 2H); 1.19 (s; 6H) |
| 62 | 5-(2-(difluoromethyl)imidazo[4,5-c]pyridin-1-yl)-2-((4-tert-butylpiperazin-1-yl)methyl)-7-(morpholin-4-yl)pyrazolo[1,5-a]pyrimidine | 2-(difluoromethyl)imidazo[4,5-c]pyridin-1-yl | 4-tert-butylpiperazin-1-yl | H | 526.3 | (CDCl₃) δ 9.26 (s; 1H); 8.60 (d; J = 5.8 Hz; 1H); 7.62 (d; J = 5.8 Hz; 1H); 7.30 (t; J = 54 Hz; 1H); 6.62 (s; 1H); 6.27 (s; 1H); 4.03-3.97 (m; 4H); 3.97-3.90 (m; 4H); 3.81 (s; 2H); 2.66 (bs; 8H); 1.08 (s; 9H) |
| 63 | 5-(2-(methoxymethyl)-benzimidazol-1-yl)-2-((4-tert-butylpiperazin-1-yl)methyl)-7-(morpholin-4-yl)pyrazolo[1,5-a]pyrimidine | 2-(methoxymethyl)benzimidazol-1-yl | 4-tert-butylpiperazin-1-yl | H | 519.3 | (CDCl₃) δ 7.87-7.81 (m; 1H); 7.76-7.70 (m; 1H); 7.38-7.32 (m; 2H); 6.59 (s; 1H); 6.53 (s; 1H); 4.88 (s; 2H); 4.01-3.95 (m; 4H); 3.91-3.85 (m; 4H); 3.81 (s; 2H); 3.46 (s; 3H); 2.66 (bs; 8H); 1.08 (s; 9H) |
| 64 | 5-(2-(difluoromethyl)benzimidazol-1-yl)-2-((3-(morpholin-4-yl)azetidin-1-yl)methyl)-7-(morpholin-4-yl)pyrazolo[1,5-a]pyrimidine | 2-(difluoromethyl)benzimidazol-1-yl | 3-(morpholin-4-yl)azetidin-1-yl | H | 525.3 | (CDCl₃) δ 7.95-7.88 (m; 1H); 7.70-7.63 (m; 1H); 7.47-7.38 (m; 2H); 7.30 (t; J = 54.0 Hz; 1H); 6.65 (s; 1H); 6.36 (s; 1H); 4.17-4.07 (m; 2H); 4.03-3.96 (m; 4H); 3.96-3.84 (m; 6H); 3.78-3.68 (m; 4H); 3.44-3.32 (m; 2H); 3.31-3.18 (m; 1H); 2.41-2.31 (m; 4H) |

TABLE 11-continued

Compounds of the invention of formula (I) wherein Y represents —CH$_2$—

| Ex. No. | Chemical name | R$^1$ | R$^2$ | R$^3$ | MS-ESI [M + H]$^+$ | $^1$H NMR (300 MHz) |
|---|---|---|---|---|---|---|
| 65 | 5-(2-(difluoromethyl)benzimidazol-1-yl)-2-((3-((2R,6S)-2,6-dimethylmorpholin-4-yl)azetidin-1-yl)methyl)-7-(morpholin-4-yl)-pyrazolo[1,5-a]pyrimidine | (2-(difluoromethyl)benzimidazol-1-yl) | 3-((2R,6S)-2,6-dimethylmorpholin-4-yl)azetidin-1-yl | H | 553.3 | (CDCl$_3$) δ 7.97-7.89 (m; 1H); 7.73-7.65 (m; 1H); 7.48-7.38 (m; 2H); 7.29 (t; J = 54.0 Hz; 1H); 6.64 (s; 1H); 6.35 (s; 1H); 4.17-4.08 (m; 2H); 4.06-3.99 (m; 2H); 3.97-3.84 (m; 6H); 3.79-3.68 (m; 4H); 3.46-3.34 (m; 2H); 3.32-3.19 (m; 1H); 2.44-2.35 (m; 4H); 1.16 (d; J = 7.0 Hz; 6H) |
| 66 | 5-(2-(difluoromethyl)benzimidazol-1-yl)-2-((3-(4,4-difluoropiperidin-1-yl)azetidin-1-yl)methyl)-7-(morpholin-4-yl)pyrazolo[1,5-a]pyrimidine | (2-(difluoromethyl)benzimidazol-1-yl) | 3-(4,4-difluoropiperidin-1-yl)azetidin-1-yl | H | 559.3 | (CDCl$_3$) δ 7.96-7.88 (m; 1H); 7.69-7.62 (m; 1H); 7.46-7.38 (m; 2H); 7.30 (t; J = 54.0 Hz; 1H); 6.55 (s; 1H); 6.32 (s; 1H); 4.02-3.95 (m; 4H); 3.94-3.87 (m; 6H); 3.69-3.60 (m; 2H); 3.14-3.03 (m; 3H); 2.49-2.37 (m; 4H); 2.09-1.92 (m; 4H) |
| 67 | 5-(2-(difluoromethyl)benzimidazol-1-yl)-2-((3-(3-methoxyazetidin-1-yl)azetidin-1-yl)methyl)-7-(morpholin-4-yl)pyrazolo[1,5-a]pyrimidine | (2-(difluoromethyl)benzimidazol-1-yl) | 3-(3-methoxyazetidin-1-yl)azetidin-1-yl | H | 525.3 | (CDCl$_3$) δ 7.97-7.88 (m; 1H); 7.69-7.62 (m; 1H); 7.47-7.39 (m; 2H); 7.31 (t; J = 54.0 Hz; 1H); 6.55 (s; 1H); 6.31 (s; 1H); 4.11-4.02 (m; 1H); 4.02-3.95 (m; 4H); 3.94-3.87 (m; 4H); 3.85 (s; 2H); 3.63-3.56 (m; 2H); 3.52-3.44 (m; 2H); 3.44-3.34 (m; 1H); 3.27 (s; 3H); 3.16-3.09 (m; 2H); 3.03-2.95 (m; 2H) |

TABLE 11-continued

Compounds of the invention of formula (I) wherein Y represents —CH$_2$—

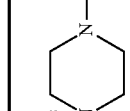

| Ex. No. | Chemical name | R$^1$ | R$^2$ | R$^3$ | MS-ESI [M + H]$^+$ | $^1$H NMR (300 MHz) |
|---|---|---|---|---|---|---|
| 68 | 5-(2-(difluoromethyl)benzimidazol-1-yl)-3-methyl-2-((4-tert-butylpiperazin-1-yl)methyl)-7-(morpholin-4-yl)pyrazolo[1,5-a]pyrimidine | 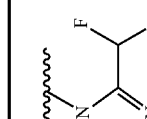 | H$_3$C–C(CH$_3$)–N(piperazine) with H$_3$C | Me | 539.3 | (CDCl$_3$) δ 7.96-7.90 (m; 1H); 7.70-7.64 (m; 1H); 7.47-7.38 (m; 2H); 7.34 (t; J = 54.0 Hz; 1H); 6.24 (s; 1H); 4.02-3.95 (m; 4H); 3.93-3.85 (m; 4H); 3.81 (s; 2H); 2.73-2.56 (m; 8H); 2.33 (s; 3H); 1.07 (s; 9H) |
| 69 | 5-(2-(difluoromethyl)benzimidazol-1-yl)-3-methyl-2-((4-(2-hydroxypropan-2-yl)piperidin-1-yl)methyl)-7-(morpholin-4-yl)pyrazolo[1,5-a]pyrimidine | 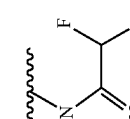 | HO–C(CH$_3$)(CH$_3$)–piperidine | Me | 540.3 | (CDCl$_3$) δ 7.98-7.88 (m; 1H); 7.72-7.63 (m; 1H); 7.49-7.37 (m; 2H); 7.35 (t; J = 54.0 Hz; 1H); 6.25 (s; 1H); 4.03-3.94 (m; 4H); 3.94-3.85 (m; 4H); 3.77 (s; 2H); 3.14-3.04 (m; 2H); 2.33 (s; 3H); 2.17-2.04 (m; 2H); 1.81-1.69 (m; 2H); 1.50-1.34 (m; 2H); 1.33-1.26 (m; 1H); 1.18 (s; 6H) |

Example 70. 2-(4-tert-butylpiperazin-1-ylcarbonyl)-5-(1H-indol-4-yl)-7-(morpholin-4-yl)pyrazolo[1,5-a]pyrimidine

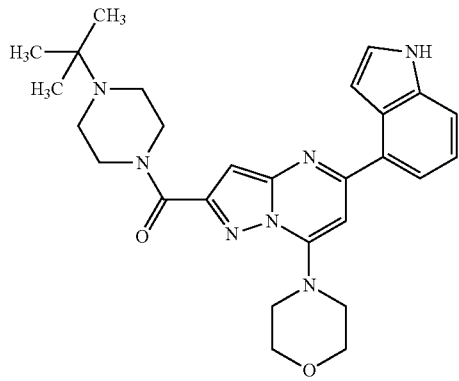 [SMILES: CC(C)(C)N1CCN(C(=O)c2cc3nc(-c4cccc5[nH]ccc45)cc(N4CCOCC4)n3n2)CC1]

To the solution of 0.545 g (1.50 mmol) of Intermediate II-10 dissolved in 15 ml of dry DMF, 0.47 g (3.3 mmol) of 1-tert-butylpiperazine, 0.446 g (3.3 mmol) of HOBt, 0.633 g (3.3 mmol) of EDCI, and 0.63 ml (0.455 g, 4.5 mmol) of TEA were added. The whole mixture was stirred at room temperature for 40 h. The mixture was added with 50 ml of water and phases were separated. Aqueous phase was extracted 3× with DCM. Combined organic phases were dried over anhydrous sodium sulphate. After filtration of the drying agent and evaporation of the solvent, the reaction mixture was separated by column chromatography (silicagel modified with propylamine) using heptane/ethyl acetate from 100/0 to 0/100 system as an eluent. After separation 0.263 g (36%) of the compound 70 were obtained. $^1$H NMR (300 MHz, CDCl$_3$) δ 8.90 (bs; 1H); 7.60 (dd; J=7.4; 0.8 Hz; 1H); 7.48 (d; J=8.1 Hz; 1H); 7.33-7.25 (m; 2H); 7.12-7.04 (m; 1H); 6.93 (s; 1H); 6.72 (s; 1H); 4.01-3.93 (m; 4H); 3.93-3.84 (m; 4H); 3.80-3.71 (m; 4H); 2.78-2,55 (m; 4H); 1.13 (s; 9H). MS-ESI: (m/z) calculated for C$_{27}$H$_{33}$N$_7$O$_2$ [M+H]$^+$: 488.28; determined 488.3.

Example 71. 5-(2-(difluoromethyl)benzimidazol-1-yl)-3-chloro-2-((4-tert-butylpiperazin-1-yl)methyl)-7-(morpholin-4-yl)pyrazolo[1,5-a]pyrimidine

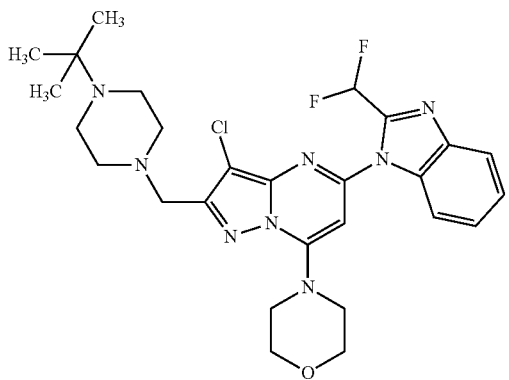 [SMILES: CC(C)(C)N1CCN(Cc2nn3c(N4CCOCC4)cc(-n4c(C(F)F)nc5ccccc54)nc3c2Cl)CC1]

To the flask 50 mg (0.095 mmol) of the compound of Example 50 were added and dissolved in 1.0 ml DCM, then 17.8 mg (0.134 mmol) of NCS (N-chloro-succinimide) were added. The whole mixture was stirred at 30° C. for 24 h and then 3 ml of sodium pyrosulphite were added. The phases were separated and aqueous phase was extracted twice with chloroform. Combined organic phases were dried over anhydrous sodium sulphate. After filtration of the drying agent and evaporation of the solvent with the evaporator, the reaction mixture was separated on chromatographic plate using as an eluent the system CHCl$_3$/MeOH—90/10. After separation 50 mg (94%) of the compound 71 were obtained. $^1$H NMR (300 MHz, CDCl$_3$) δ 7.97-7.89 (m; 1H); 7.74-7.66 (m; 1H); 7.49-7.39 (m; 2H); 7.37 (t; J=54 Hz; 1H); 6.36 (s; 1H); 4.00-3.91 (m; 10H); 2.78-2.57 (m; 8H); 1.07 (s; 9H). MS-ESI: (m/z) calculated for C$_{279}$H$_{33}$ClF$_2$N$_8$O [M+H]$^+$: 559.25; determined 559.3.

Example 72. 5-(2-(difluoromethyl)benzimidazol-1-yl)-3-bromo-2-((4-tert-butylpiperazin-1-yl)methyl)-7-(morpholin-4-yl)pyrazolo[1,5-a]pyrimidine Obtained analogously as the compound of Example 71, replacing N-chloro-succinimide with NCB (N-bromosuccinimide). $^1$H NMR (300 MHz, CDCl$_3$) δ 7.97-7.89 (m; 1H); 7.74-7.66 (m; 1H); 7.49-7.39 (m; 2H); 7.38 (t; J=54 Hz; 1H); 6.40 (s; 1H); 4.01-3.92 (m; 10H); 2.77-2.56 (m; 8H); 1.07 (s; 9H). MS-ESI: (m/z) calculated for C$_{28}$H$_{33}$BrF$_2$N$_8$O [M+H]$^+$: 602.20; determined 602.2.

Biological Activity of the Compounds of the Invention

Test of PI3K Kinases Inhibition In Vitro

The effects of the compounds of the invention were analyzed in vitro using PI3K kinases inhibition assay described below.

Tested compounds were dissolved in 100% DMSO, and thus obtained solutions were serially diluted in 1× reaction buffer. Recombinant kinase was diluted in a reaction mixture comprising 5× reaction buffer, substrate (1 mM sodium diacetate 4,5-bisphosphate phosphatydylinositol (PIP2) solution in 40 mM Tris buffer), and water. To the wells in a 96-wells plate, 5 µl of compounds solutions and 15 µl of the kinase solution in the reaction mixture were added. To initiate interaction of tested chemical compounds with the enzyme, the plate was incubated for 10 minutes at suitable temperature in a plate thermostat with orbital shaking at 600 rpm. Negative control wells contained all above reagents except tested compound and kinase, and positive control wells contained all above reagents except tested compounds. Enzymatic reaction was initiated by adding 5 µl of 150 µM ATP solution, subsequently the plate was incubated for 1 hour at 25° C. or 30° C. (depending on PI3K isoform tested) in plate thermostat with orbital shaking of the plate contents at 600 rpm. Reaction conditions are presented below in Table 12.

TABLE 12

| KINASE | Kinase concentration [ng per reaction] | Reaction temperature and time | Substrate PIP2 [final concentration μM] | Reaction buffer |
|---|---|---|---|---|
| PI3Kα (Carna Biosciences) | 7.5 ng | 25° C., 1 h | 30 μM | 50 mM HEPES pH 7.5<br>50 mM NaCl<br>3 mM MgCl$_2$<br>0.025 mg/ml BSA |
| PI3Kδ (Merck Millipore) | 10 ng | 25° C., 1 h | 30 μM | 50 mM HEPES pH 7.5<br>50 mM NaCl<br>3 mM MgCl$_2$<br>0.025 mg/ml BSA |
| PI3Kβ (Merck Millipore) | 15 ng | 30° C., 1 h | 50 μM | 50 mM HEPES pH 7.5<br>50 mM NaCl<br>3 mM MgCl$_2$<br>0.025 mg/ml BSA |
| PI3Kγ (Merck Millipore) | 30 ng | 30° C., 1 h | 50 μM | 40 nM Tris pH 7.5<br>20 mM MgCl$_2$<br>0.1 mg/ml BSA<br>1 mM DTT |

Detection of ADP formed in the enzymatic reaction was then performed using ADP-Glo Kinase Assay (Promega). To the wells of a 96-well plate 25 μl of ADP-Glo Reagent were added, and the plate was incubated for 40 minutes at 25° C. in a plate thermostat with orbital shaking at 600 rpm. Then to the wells of 96-well plate 50 μl of Kinase Detection Reagent were added and the plate was incubated for 40 minutes at 25° C. in a plate thermostat with orbital shaking at 600 rpm. After incubation time, luminescence intensity in a well was measured by Victor Light luminometer (Perkin Elmer, Inc.).

IC$_{50}$ values were determined on the basis of luminescence intensity measurements in wells containing tested compounds at different concentrations and in control wells. These values were calculated with Graph Pad 5.03 software by fitting the curve using non-linear regression. Each compound was tested at least in quadruplicates (4 wells) on two 96-well plates using at least 4 wells of each of the controls.

Averaged results of inhibition activity with respect to specific isoforms of PI3K kinases for selected compounds of the invention are presented as IC$_{50}$ in Table 13 below. In Table 13, symbols A, B and C have the following meanings:

TABLE 13

| Ex. No. | PI3Kα | PI3Kβ | PI3Kγ | PI3Kδ |
|---|---|---|---|---|
| 1 | C | C | B | A |
| 2 | C | n.d. | n.d. | B |
| 3 | C | n.d. | n.d. | A |
| 4 | C | C | C | A |
| 5 | C | C | C | A |
| 6 | C | n.d. | n.d. | B |
| 7 | C | C | C | A |
| 8 | C | C | C | A |
| 9 | C | C | C | A |
| 10 | C | C | C | A |
| 11 | C | C | C | A |
| 12 | C | n.d. | n.d. | A |
| 13 | C | C | C | A |
| 14 | C | n.d. | n.d. | A |
| 15 | C | n.d. | n.d. | B |
| 16 | C | C | C | A |
| 17 | C | C | C | A |
| 18 | C | n.d. | n.d. | B |
| 19 | C | C | C | A |
| 20 | C | C | n.d. | A |
| 21 | C | n.d. | n.d. | B |
| 22 | C | C | C | A |
| 23 | C | n.d. | n.d. | B |
| 24 | C | n.d. | n.d. | B |
| 25 | C | C | C | A |
| 26 | C | n.d. | n.d. | A |
| 27 | C | n.d. | n.d. | A |
| 28 | C | C | C | A |
| 29 | C | C | n.d. | A |
| 30 | C | C | C | A |
| 31 | C | C | C | A |
| 32 | C | C | n.d. | A |
| 33 | C | C | C | A |
| 34 | C | n.d. | n.d. | A |
| 35 | C | C | C | A |
| 36 | C | n.d. | n.d. | A |
| 37 | n.d. | n.d. | n.d. | B |
| 38 | C | n.d. | n.d. | B |
| 42 | C | n.d. | n.d. | B |
| 43 | C | n.d. | n.d. | B |
| 47 | C | n.d. | n.d. | A |
| 48 | C | n.d. | n.d. | B |
| 49 | C | n.d. | n.d. | B |
| 50 | B | C | C | A |
| 51 | C | C | C | A |
| 52 | C | n.d. | n.d. | B |
| 53 | C | n.d. | n.d. | B |
| 54 | C | n.d. | n.d. | B |
| 55 | C | n.d. | n.d. | B |
| 62 | C | C | C | B |
| 64 | B | C | C | A |
| 65 | n.d. | n.d. | n.d. | A |
| 66 | B | C | C | A |
| 67 | n.d. | n.d. | n.d. | A |
| 68 | B | C | C | A |
| 69 | B | C | C | A |
| 70 | C | C | C | A |
| 71 | B | C | C | A |

A: IC$_{50}$ <100 nM;
B: 100 nM ≤ IC$_{50}$ < 1000 nM;
C: IC$_{50}$ ≥1000 nM
n.d.—not determined Test of AKT Protein Phosphorylation Level by Western Blot The AKT protein phosphorylation level in a cell depends on the activity of PI3K pathway—inhibition of PI3K kinases with an inhibitor (tested compound) results in decrease of AKT phosphorylation that can be seen in a Western blot method as disappearance of a lane stained with anti-pAKT antibodies. Inhibition of kinases does not influence the total protein level; staining with anti-pAKT antibodies is a control in the experiment. Control for each staining is the measurement of the level of glyceraldehyde 3-phosphate dehydrogenase (GAPDH), the protein present in cells in a constant amount.

As a cell model for testing AKT phosphorylation level by PI3Kδ, RAJI cell line (origin: Burkitt lymphoma, supplier: ATCC) stimulated with IgM antibody was used. This antibody, by binding with BCR receptor present on a surface of these cells, causes PI3Kδ activation and in turn increase of AKT phosphorylation (Winkler et al. 2013, Chemistry and Biology).

As a cell model for testing AKT phosphorylation level by PI3Kγ, RAW264.7 cell line (origin: Ab-MLB transformed murine lymphocytes line, supplier: ATCC), stimulated with C5a component of the complement system. This protein, by binding with C5aR receptor, causes activation of PI3Kγ, this in turn resulting in increase of AKT phosphorylation level (Winkler et al. 2013, Chemistry and Biology).

Cells were seeded onto 6-well plates at a density 1-1.5× $10^6$/ml in a culture without inhibitor. Directly after seeding cells were treated with tested compounds for 1 hour, and then cells were stimulated (Raji: anti-IgM, 5 mg/ml, 15 min before the end of incubation; RAW: C5a, 5 ng/ml, 5 min before the end of incubation). Then the cells were lysed with RIPA buffer (Sigma-Aldrich) containing proteases inhibitors (Halt Protease Inhibitor Cocktail, Thermo) and phosphatases (PhosSTOP, Roche) and protein concentration was determined using BCA method (Pierce) in accordance with manufacturer's recommendations. Obtained lysates were subjected to SDS-PAGE electrophoresis for 2 hours at 100 V in Mini Protean III (BioRad) apparatus. Following electrophoresis, separated proteins were transferred onto nitrocellulose membrane by electrotransfer technique for 1 hour at 100 V in Mini Protean III apparatus. Western blot analysis of selected proteins was performed in accordance with antibodies manufacturer's recommendations.

Primary antibodies used were anti-pAKT and anti-AKT (Cell Signaling Technology) and anti-GAPDH (Millipore). For detection of primary antibodies, secondary antibodies coupled with horseradish peroxidase (Sigma-Aldrich) were used. Membrane-bound proteins were visualized with LumiLight reagent (Roche), and then developed on Light Film BioMax films (Kodak).

Figure 2:
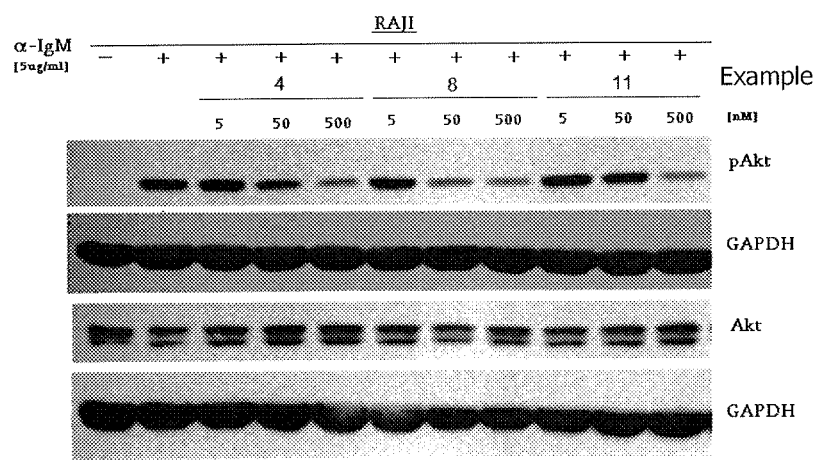
Figure 3:
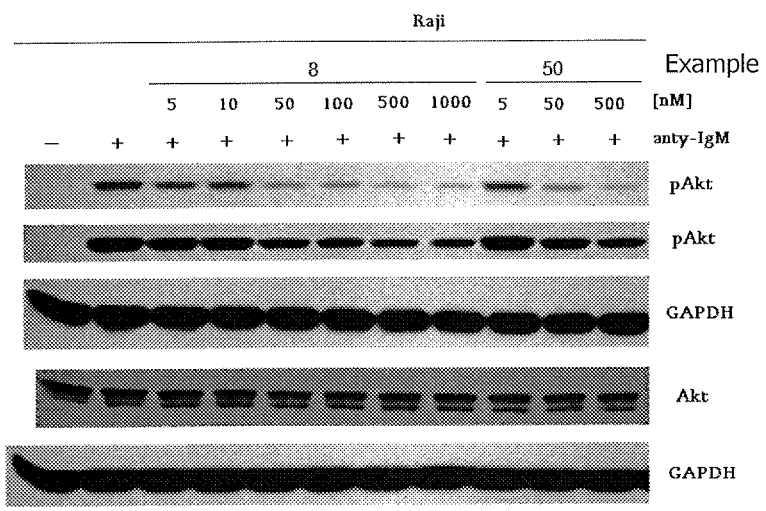
Figure 4:
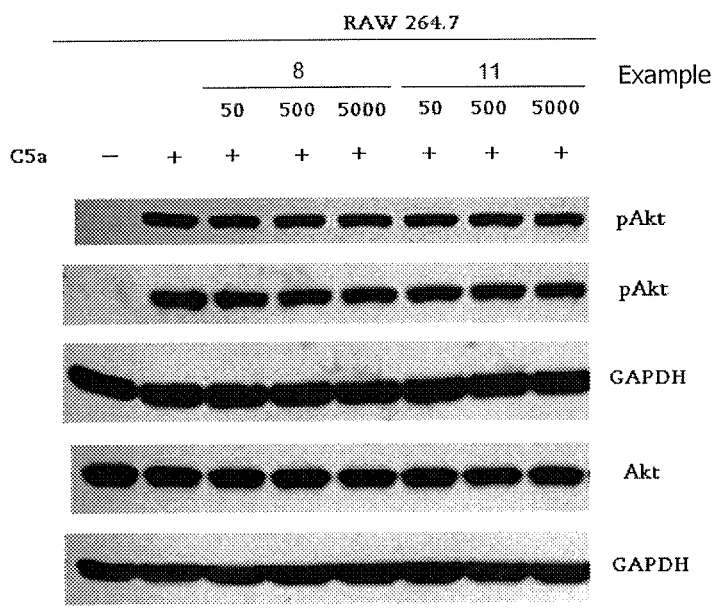

Results of determination of the level of phosphorylated AKT (pAKT) and total AKT in cells treated for 1 hour with selected compounds of the invention are presented on a Drawing, on FIGS. 1 to 3 for PI3Kδ, and for PI3Kγ on FIG. 4. FIG. 3 shows dose-dependent decrease of PI3K delta activity as a decreasing intensity of a lane for phospho-AKT protein (line RAJI). Experiments performed on RAW line, wherein AKT protein is phosphorylated by kinase PI3K gamma, do not show decrease of the amount of phosphorylated AKT what confirms selective action of the compounds on PI3K delta kinase.

Pharmacokinetics Testing In Vivo

To test bioavailability of the compounds of the invention, their pharmacokinetic properties were studied in vivo on rats in accordance with methodology described below.

Tests were performed on about 12 weeks old Wistar rats, weight 250-300 g. Rats were given orally tested compounds at 30 mg/kg m.c. Blood samples were collected from animals for analysis in 6 time points—30 min, 1 h, 2 h, 4 h, 7 h, and 12 h from administration of the compound. Blood was collected to tubes with K2EDTA and centrifuged for 15 min, 2000×g, at room temperature to separate serum. Collected serum samples were maintained at −20° C. before analysis. Each of the compounds was tested on a group of 5 animals.

Serum concentrations of tested compounds were determined by spectrophotometry. For each of tested compounds, time to reach maximum serum concentration (Tmax), maximum concentration (Cmax), and area under the curve (AUC) were determined. Pharmacokinetic parameters for four representative compounds of the present invention are presented in Table 14:

TABLE 14

| | Example No. | | | |
|---|---|---|---|---|
| | 4 | 8 | 11 | 50 |
| Tmax [h] | 2 | 2 | 2 | 2 |
| Cmax [ng/ml] | 600 | 200 | 300 | 900 |
| AUC [mg * h/L] | 3.58 | 1.29 | 1.25 | 5.03 |

Tested compounds are bioavailable and reach Tmax and Cmax typical for medicaments in this class.

The invention claimed is:

1. A compound of the general formula (I)

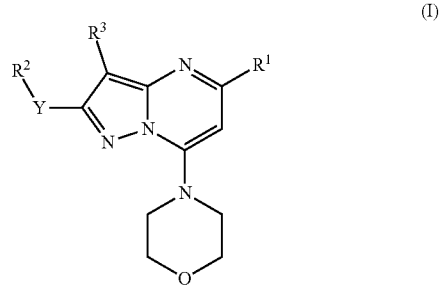

wherein:

Y represents —$CH_2$- or >C=O;

$R^1$ is selected from the group consisting of A1, A2 and A3:

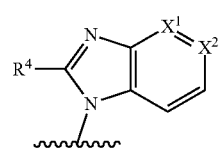

A1

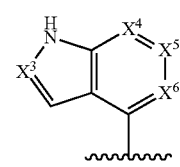

A2

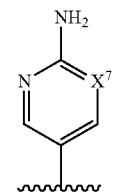

A3

$R^2$ represents:

dioxothiomorpholino moiety B1;

piperazinyl moiety B2

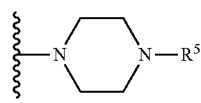

wherein two carbon atoms of the piperazine ring can be optionally joined with methylene bridge —$CH_2$— to form 2,5-diazabicyclic moiety, and $R^5$ is selected from the group consisting of —$SO_2CH_3$; —C(O)—C1-C3-alkyl, —C(O)—C3-C5-cycloalkyl; phenyl substituted with —O—C1-C3 alkyl; and —$CR^6R^7R^8$, wherein $R^6$, $R^7$ and $R^8$ independently represent hydrogen atom, $CH_3$, cyclopropyl or $CONH_2$, with the proviso that only one of $R^6$, $R^7$ and $R^8$ can represent cyclopropyl or $CONH_2$, or one of $R^6$, $R^7$ and $R^8$ represents hydrogen atom and remaining two of $R^6$, $R^7$ and $R^8$ are joined together to form —$(CH_2)_2$, —$(CH_2)_3$, —$(CH_2)_4$, or —$(CH_2$—O—$CH_2)$— group;

azetidinyl moiety B3

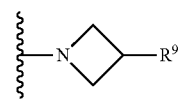

wherein $R^9$ is selected from the group consisting of morpholino, 2,6-dimethylomorpholino, 1,1-dioxothiomorpholino, 4,4-difluoropiperidynyl and 3-methoxyazetidin-1-yl; or piperidinyl moiety B4

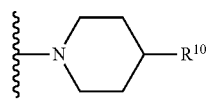

wherein $R^{10}$ is selected from the group consisting of C1-C4 alkyl; C1-C4 alkyl substituted with OH; —COO(C1-C3 alkyl); —N(C1-C3 alkyl)$_2$; —NHCONH—C1-C3-alkyl; —NHCONH—C1-C3-phenyl; piperazinyl; and piperazinyl substituted at the position 4 with C1-C3 alkyl;

$R^3$ is selected from the group consisting of H, halogen, and C1-C4 alkyl;

$R^4$ is selected from the group consisting of C1-C4 alkyl, C3-C4-cycloalkyl, C1-C4 alkyl substituted with C1-C4 alkoxy, and $CHF_2$;

$X^1$ and $X^2$ have the following meanings:
(i) $X^1$ represents CH and $X^2$ represents CH or N;
(ii) $X^1$ represents N and $X^2$ represents CH, or
(iii) $X^1$ represents CH and $X^2$ represents C—O—$CH_3$;

$X^3$, $X^4$, $X^5$ and $X^6$ have the following meanings:
(i) $X^3$ represents N, $X^4$ represents CH, $X^5$ represents CH, and $X^6$ represents CH;
(ii) $X^3$ represents CH, $X^4$ represents N, $X^5$ represents CH, and $X^6$ represents CH;
(iii) $X^3$ represents CH, $X^4$ represents CH, $X^5$ represents N, and $X^6$ represents CH;
(iv) $X^3$ represents CH, $X^4$ represents CH, $X^5$ represents CH, and $X^6$ represents CH or CF; or
(v) $X^3$ represents CH, $X^4$ represents CH, $X^5$ represents CF, and $X^6$ represents CH;

$X^7$ represents CH or N;

wavy line indicates the point of attachment;

or pharmaceutically acceptable salts thereof.

2. The compound according to claim 1, wherein Y represents —$CH_2$—.

3. The compound according to claim 1, wherein Y represents >C=O.

4. The compound according to claim 2, wherein $R^3$ represents H.

5. The compound according to claim 1, wherein $R^3$ represents C1-C4 alkyl.

6. The compound according to claim 1, wherein $R^3$ represents halogen.

7. The compound according to claim 2, wherein $R^1$ represents A1 or A2.

8. The compound according to claim 1, wherein $R^1$ represents A3.

9. The compound according to claim 1, wherein $R^2$ represents B1.

10. The compound according to claim 2, wherein $R^2$ represents B2.

11. The compound according to claim 1, wherein $R^2$ represents B3.

12. The compound according to claim 1, wherein $R^2$ represents B4.

13. A pharmaceutical composition comprising the compound of formula (I) as defined in claim 1 and pharmaceutically acceptable excipients.

14. A method of PI3 kinase inhibition in a subject, the method comprises administering to the subject in need thereby an amount of the compound of formula (I) as defined in claim 1 effective to inhibit PI3 kinase in the subject.

15. The compound according to claim 1 wherein Y represents —$CH_2$—; $R^1$ represents A1 or A2; $R^2$ represents B2; and $R^3$ represents H.

16. The compound according to claim 1 wherein Y represents —$CH_2$—; $R^1$ represents A1 wherein $X^1$ represents CH and $X^2$ represents CH; $R^2$ represents B2; and $R^3$ represents H.

17. The compound according to claim 16 which is 5-(2-(difluoromethyl)benzimidazol-1-yl)-2-((4-tert-butylpiperazin-1-yl)methyl)-7-(morpholin-4-yl)pyrazolo[1,5-a]pyrimidine or a pharmaceutically acceptable salt thereof.

18. The compound according to claim 1 wherein Y represents —$CH_2$—; $R^1$ represents A2 wherein $X^3$ represents N, $X^4$ represents CH, $X^5$ represents CH, and $X^6$ represents CH; R2 represents B2; and R3 represents H.

19. The compound according to claim 1 which is 5-(1H-6-azaindol-4-yl)-2-((4-tert-butylpiperazin-1-yl)methyl)-7-(morpholin-4-yl)-pyrazolo[1,5-a]pyrimidine.

* * * * *